(12) United States Patent
Soares et al.

(10) Patent No.: US 12,394,044 B2
(45) Date of Patent: Aug. 19, 2025

(54) INFORMATION PROCESSING SYSTEM, INFORMATION PROCESSING DEVICE, INFORMATION PROCESSING METHOD, AND PROGRAM

(71) Applicants: NIKON CORPORATION, Tokyo (JP); Optos plc, Dunfermline Fife (GB)

(72) Inventors: Devin Soares, Marlborough, MA (US); Branden Coleman, Marlborough, MA (US); Bradley Yates, Marlborough, MA (US); Naoyuki Kawachi, Tokyo (JP)

(73) Assignees: NIKON CORPORATION, Tokyo (JP); OPTOS PLC, Dunfermline Fife (GB)

( * ) Notice: Subject to any disclaimer, the term of this patent is extended or adjusted under 35 U.S.C. 154(b) by 522 days.

(21) Appl. No.: 17/631,275

(22) PCT Filed: Jul. 29, 2020

(86) PCT No.: PCT/JP2020/029055
§ 371 (c)(1),
(2) Date: Jan. 28, 2022

(87) PCT Pub. No.: WO2021/020442
PCT Pub. Date: Feb. 4, 2021

(65) Prior Publication Data
US 2022/0261989 A1 Aug. 18, 2022

Related U.S. Application Data
(60) Provisional application No. 62/880,980, filed on Jul. 31, 2019.

(51) Int. Cl.
*G06T 7/00* (2017.01)
*A61B 3/10* (2006.01)
(Continued)

(52) U.S. Cl.
CPC ............ *G06T 7/0012* (2013.01); *A61B 3/102* (2013.01); *A61B 3/12* (2013.01); *A61B 3/14* (2013.01);
(Continued)

(58) Field of Classification Search
CPC ...... G06T 7/0012; G16H 30/20; G16H 50/20; A61B 3/102; A61B 3/12; A61B 3/14
See application file for complete search history.

(56) References Cited

U.S. PATENT DOCUMENTS

2014/0276025 A1* 9/2014 Durbin ................. A61B 3/0025
600/407
2015/0070469 A1* 3/2015 Yoshibayashi ....... G01B 11/002
348/46
(Continued)

FOREIGN PATENT DOCUMENTS

JP 2002-329190 A 11/2002
JP 5951086 B2 7/2016
(Continued)

OTHER PUBLICATIONS

International Search Report with English translation and Written Opinion issued in corresponding application No. PCT/JP2020/029055 dated Oct. 27, 2020.
(Continued)

*Primary Examiner* — David Bilodeau
(74) *Attorney, Agent, or Firm* — Foley & Lardner LLP

(57) ABSTRACT

An information processing system comprises: an image acquisition device acquiring subject eye image data of a patient; and a first information processing device communicating with the image acquisition device and storing the image data, the image acquisition device transmits, to the first information processing device, the image data and first transmission data including additional information used to
(Continued)

identify an image diagnosis device performing image diagnosis on the image data, the first information processing device: stores the image data when receiving the first transmission data from the image acquisition device; identifies, based on the additional information, a first image diagnosis device performing a first image diagnosis on the image data and/or a second image diagnosis device performing a second image diagnosis differing from the first image diagnosis on the image data; and transmits second transmission data including the image data to the identified image diagnosis device.

13 Claims, 12 Drawing Sheets

(51) Int. Cl.
    *A61B 3/12*     (2006.01)
    *A61B 3/14*     (2006.01)
    *G16H 30/20*     (2018.01)
    *G16H 50/20*     (2018.01)

(52) U.S. Cl.
    CPC ............. *G16H 30/20* (2018.01); *G16H 50/20* (2018.01); *G06T 2207/30041* (2013.01); *G06T 2207/30096* (2013.01)

(56) References Cited

U.S. PATENT DOCUMENTS

| | | | |
|---|---|---|---|
| 2015/0092161 A1* | 4/2015 | Akita | A61B 3/0025 351/206 |
| 2015/0313578 A1* | 11/2015 | Yu | A61B 8/4254 600/459 |
| 2017/0196458 A1* | 7/2017 | Ternes | A61B 7/023 |
| 2019/0065897 A1* | 2/2019 | Li | G06F 18/2415 |
| 2019/0221313 A1* | 7/2019 | Rim | G06F 18/217 |
| 2020/0075162 A1* | 3/2020 | Kovalan | G16H 40/20 |
| 2020/0085290 A1* | 3/2020 | Wang | A61B 3/12 |
| 2020/0160521 A1* | 5/2020 | Wang | G06V 40/193 |
| 2022/0058796 A1* | 2/2022 | Vaghefi Rezaei | A61B 3/0025 |
| 2022/0165416 A1* | 5/2022 | Kang | G16H 50/20 |
| 2022/0165418 A1* | 5/2022 | Li | G06V 10/7747 |

FOREIGN PATENT DOCUMENTS

| | | |
|---|---|---|
| JP | 2018-013826 A | 1/2018 |
| JP | 2018-014058 A | 1/2018 |
| WO | WO-2018/201632 A1 | 11/2018 |
| WO | WO-2018/201633 A1 | 11/2018 |
| WO | WO-2020/200087 A1 | 10/2020 |

OTHER PUBLICATIONS

Extended European Search Report issued in corresponding European Patent Application No. 20848309.9, dated Jul. 20, 2023 (12 pages).
CN First Office Action issued in Corresponding Chinese Patent Application No. 202080068885.2 Dated Oct. 31, 2024 (24 pages).
Notice of Reasons for Refusal issued in Japanese Application No. 2024-160469, dated Jun. 17, 2025.

* cited by examiner

INFORMATION PROCESSING SYSTEM, INFORMATION PROCESSING DEVICE, INFORMATION PROCESSING METHOD, AND PROGRAM

CROSS-REFERENCE TO RELATED APPLICATIONS

The present application is a national stage entry of PCT/JP2020/029055, filed on Jul. 29, 2020, which claims priority from U.S. provisional application 62/880,980 filed on Jul. 31, 2019, the contents of all of which are hereby incorporated by reference in their entirety.

TECHNICAL FIELD

The present invention relates to an information processing system, an information processing device, an information processing method, and a program

BACKGROUND

A known ophthalmological information processing server can perform ophthalmological image analysis (see Patent Document 1). However, conventionally, selecting an appropriate ophthalmological information processing server according to the device that captures the image or the entity that has requested image analysis is not considered.

PRIOR ART

Patent Document
[Patent Document 1] JP 5951086 B

SUMMARY OF THE INVENTION

An information processing system which is an aspect of the present invention disclosed in the present application comprises: an image acquisition device configured to acquire subject eye image data of a patient; and a first information processing device which can communicate with the image acquisition device and stores the subject eye image data, the image acquisition device performs first transmission processing of transmitting, to the first information processing device, the subject eye image data and first transmission data which includes additional information used to identify an image diagnosis device configured to perform image diagnosis on the subject eye image data, the first information processing device performs: storage processing of storing the subject eye image data when the first transmission data is received from the image acquisition device; identification processing of identifying, on the basis of the additional information, at least one of a first image diagnosis device that performs a first image diagnosis on the subject eye image data and a second image diagnosis device that performs a second image diagnosis different to the first image diagnosis on the subject eye image data; and second transmission processing of transmitting second transmission data including the subject eye image data to the identified image diagnosis device.

An information processing system which is an aspect of the present invention disclosed in the present application comprises: an image acquisition device configured to acquire subject eye image data of a patient; and a first information processing device which can communicate with the image acquisition device and stores the subject eye image data, the image acquisition device performs first transmission processing of transmitting the subject eye image data and first transmission data which includes additional information used to identify artificial intelligence configured to perform image diagnosis on the subject eye image data to the first information processing device, the first information processing device performs: storage processing of storing the subject eye image data when the first transmission data is received from the image acquisition device; identification processing of identifying, on the basis of the additional information, at least one of a first type of artificial intelligence for performing a first image diagnosis on the subject eye image data and a second type of artificial intelligence for performing a second image diagnosis different to the first image diagnosis on the subject eye image data; and second transmission processing of transmitting second transmission data including the subject eye image data and identifying information for identifying artificial intelligence to an image diagnosis device including the at least one of the first type of artificial intelligence and the second type of artificial intelligence.

An information processing device which is an aspect of the present invention disclosed in the present application comprises: a processor; and a memory device, wherein the memory device holds: subject eye image data of a patient; additional information of the subject eye image data; and correspondence information between the additional information and an image diagnosis device, wherein the processor: identifies, on the basis of the correspondence information and the additional information, at least one of a first image diagnosis device that performs a first image diagnosis on the subject eye image data and a second image diagnosis device that performs a second image diagnosis different to the first image diagnosis on the subject eye image data; and transmits transmission data including the subject eye image data to the identified image diagnosis device.

An information processing device which is an aspect of the present invention disclosed in the present application comprises: a processor; and a memory device, wherein the memory device holds: subject eye image data of a patient; additional information of the subject eye image data; and correspondence information between the additional information and an image diagnosis device, wherein the processor: identifies, on the basis of the correspondence information and the additional information, at least one of a first type of artificial intelligence for performing a first image diagnosis on the subject eye image data and a second type of artificial intelligence for performing a second image diagnosis different to the first image diagnosis on the subject eye image data; and transmits second transmission data including the subject eye image data and identifying information for identifying artificial intelligence to an image diagnosis device including the at least one of the first type of artificial intelligence and the second type of artificial intelligence.

A method for processing information which is an aspect of the present invention disclosed in the present application is performed by an information processing device, the information processing device comprises: a processor; and a memory device, wherein the memory device holds: subject eye image data of a patient; additional information of the subject eye image data; and correspondence information between the additional information and an image diagnosis device, the method comprises: identifying, by the processor, on the basis of the correspondence information and the additional information, at least one of a first image diagnosis device that performs a first image diagnosis on the subject eye image data and a second image diagnosis device that performs a second image diagnosis different to the first image diagnosis on the subject eye image data; and transmitting, by the processor, transmission data including the subject eye image data to the identified image diagnosis device.

A method for processing information which is an aspect of the present invention disclosed in the present application is performed by an information processing device, the information processing device comprises: a processor; and a memory, wherein the memory holds: subject eye image data of a patient; additional information of the subject eye image data; and correspondence information between the additional information and an image diagnosis device, the method comprises: identifying, by the processor, on the basis of the correspondence information and the additional information, at least one of a first type of artificial intelligence for performing a first image diagnosis on the subject eye image data and a second type of artificial intelligence for performing a second image diagnosis different to the first image diagnosis on the subject eye image data; and transmitting, by the processor, second transmission data including the subject eye image data and identifying information for identifying artificial intelligence to an image diagnosis device including the at least one of the first type of artificial intelligence and the second type of artificial intelligence.

A computer program which is an aspect of the present invention disclosed in the present application cases an information processing device to perform information processing, the information processing device comprising: a processor; and a memory device, wherein the memory device holds: subject eye image data of a patient; additional information of the subject eye image data; and correspondence information between the additional information and an image diagnosis device, the computer program causes the information processing device to identify, on the basis of the correspondence information and the additional information, at least one of a first image diagnosis device that performs a first image diagnosis on the subject eye image data and a second image diagnosis device that performs a second image diagnosis different to the first image diagnosis on the subject eye image data; and transmit transmission data including the subject eye image data to the identified image diagnosis device.

A computer program which is an aspect of the present invention disclosed in the present application causes an information processing device to perform information processing, the information processing device comprises: a processor; and a memory, wherein the memory holds: subject eye image data of a patient; additional information of the subject eye image data; and correspondence information between the additional information and an image diagnosis device, the computer program causes the information processing device to: identify, on the basis of the correspondence information and the additional information, at least one of a first type of artificial intelligence for performing a first image diagnosis on the subject eye image data and a second type of artificial intelligence for performing a second image diagnosis different to the first image diagnosis on the subject eye image data; and transmit second transmission data including the subject eye image data and identifying information for identifying artificial intelligence to an image diagnosis device including the at least one of the first type of artificial intelligence and the second type of artificial intelligence.

BRIEF DESCRIPTIONS OF DRAWINGS

The present invention can be appreciated by the description which follows in conjunction with the following figures, wherein.

DETAILED DESCRIPTION OF THE PREFERRED EMBODIMENTS

Figure 1:
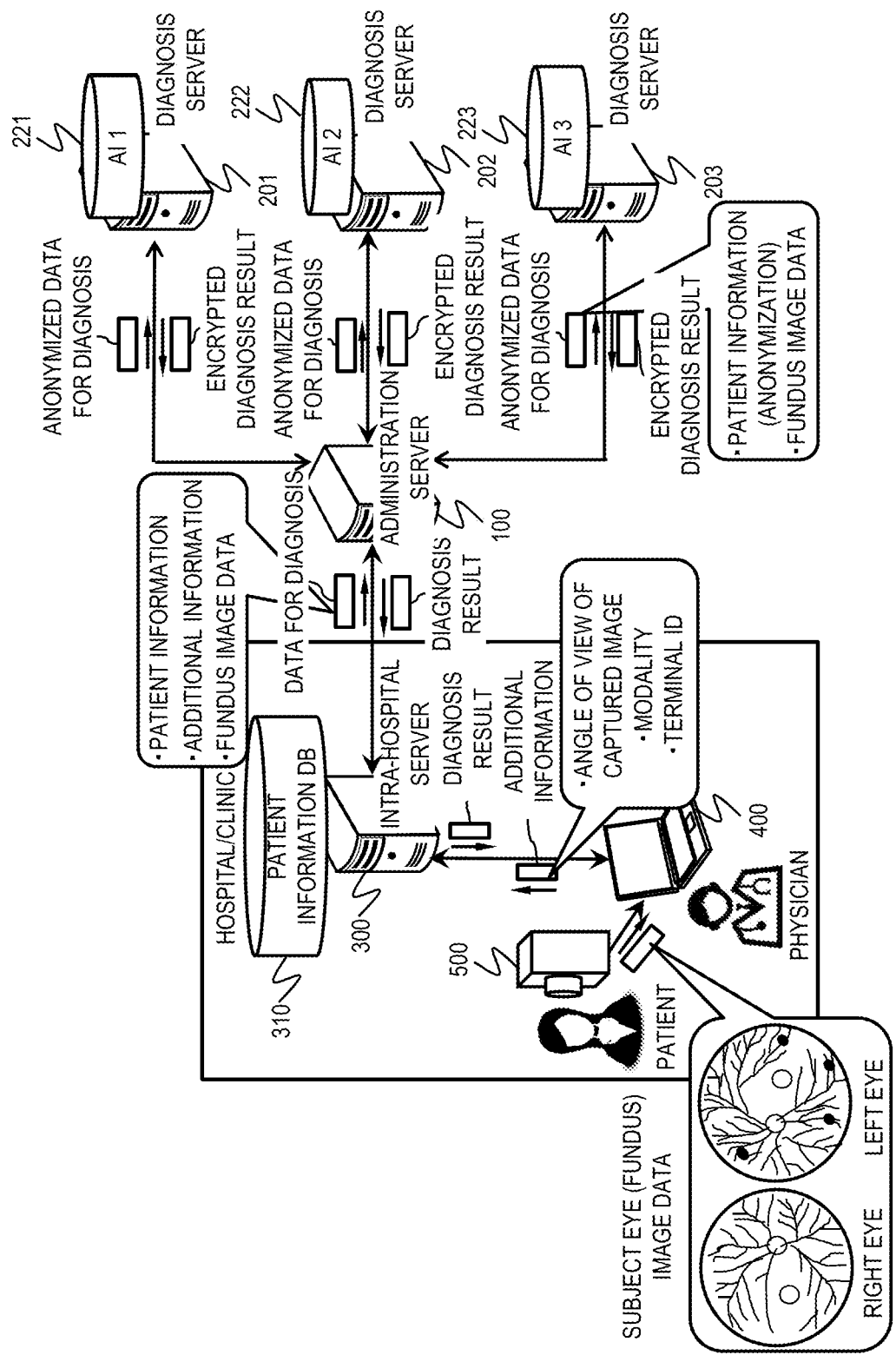
FIG. 1 is a is a diagram illustrating a configuration example of an image diagnosis system according to the first embodiment.

Hereinafter, embodiments of the invention are described in detail with reference to the accompanying drawings. It should be noted that the present embodiments are merely examples for implementing the present inventions, and do not limit the technical scope of the present inventions. In drawings, same components are denoted by same reference numerals in principle, and a repetitive description thereof is omitted.

First Embodiment

FIG. 1 is a diagram illustrating a configuration example of an image diagnosis system according to the first embodiment. The image diagnosis system includes an administration server 100, a diagnosis server 201, a diagnosis server 202, and a diagnosis server 203. The image diagnosis system also includes an intra-hospital server 300, a terminal 400, and an imaging device 500 installed in a hospital, a clinic or a diagnostic facility. The intra-hospital server 300, the terminal 400, and the imaging device 500 are connected to each other via a network.

The imaging device 500 is an ophthalmological device configured to image a fundus and examples thereof include a fundus camera, a scanning laser ophthalmoscope and an optical coherence tomography machine. The imaging device 500 is connected to the terminal 400. The imaging device 500 images the eyes of a patient and generates fundus image data for the right eye and the left eye of the patient. The generated fundus image data is sent to the terminal 400.

The fundus image data may be any one of fundus image data captured by a fundus camera, fundus image data of a fundus captured by a scanning laser ophthalmoscope, or tomographic data of a fundus captured by an optical coherence tomography machine. Alternatively, the fundus image data may be a fundus image dataset comprised of a combination of two or more of the above-described types of data. The fundus image data is an example of patient eye image data.

The terminal 400 is an example of an image acquisition device and is a computer such as a personal computer or a tablet used by a physician or the operator of an ophthalmological device. The terminal 400 is connected to the intra-hospital server 300. The terminal 400 sends data including the fundus image data and additional information, which is an example of first transmission data, to the intra-hospital server 300.

The additional information is any one of device information related to the performance or specifications of the imaging device 500, facility information including the department (ophthalmology, internal medicine, diabetic tract medicine, etc.) of the hospital or clinic in which the terminal 400 is used, prices of diagnostic plans and the names of physicians, and diagnostic type information including diagnostic modes and names of diseases to be diagnosed. Further, the additional information may be a combination of any of the above-described information. Image attribute information including the angle, modality and resolution of the image (patient eye image) captured by the imaging device 500, the model number of the imaging device 500 and a terminal ID is an example of the device information. "Modality" is information indicating the type of the imaging device 500 (e.g., fundus camera, scanning laser ophthalmoscope, optical coherence tomography machine, etc.) or the type of image (e.g., fundus image or angiogram captured by red laser or near-infrared laser) used as a medical image captured by the imaging device 500. The name of the physician or hospital using the terminal 400 and the installation location of the terminal (information related to department, e.g., ophthalmology, internal medicine or diabetic tract medicine, or information related to facility, e.g., optical retailer or diagnostic facility) is an example of the facility information.

The intra-hospital server 300, which is an example of an image acquisition device, includes a patient information database (DB) 310 that holds patient information and stores patient information received from the terminal 400 in the patient information DB 310. The intra-hospital server 300 is connected to the administration server 100 via a network. The intra-hospital server 300 includes the patient information, fundus image data and additional information received from the terminal 400 in data for diagnosis and sends the data for diagnosis, which is an example of first transmission data, to the administration server 100. The patient information in the data for diagnosis and the additional information may be partly or wholly generated by the intra-hospital server 300.

The administration server 100, which is an example of a first information processing device, generates anonymized data for diagnosis, which is an example of second transmission data and is the data for diagnosis received from the intra-hospital server 300 in which some information (e.g., patient information) has been anonymized. The administration server 100 is connected to the diagnosis server 201, the diagnosis server 202, and the diagnosis server 203 via a network. The administration server 100 selects either the diagnosis server 201, the diagnosis server 202, or the diagnosis server 203 as a diagnosis server for performing image analysis on the fundus image data included in the anonymized data for diagnosis based on the additional information, and sends the anonymized data for diagnosis to the selected diagnosis server.

The diagnosis servers 201 to 203, which are each an example of an image diagnosis device, are equipped with artificial intelligence (AI) for performing image analysis on the fundus image data. An AI1, an AI2 and an AI3 included in the diagnosis servers 201 to 203 have different respective functions (algorithms) (described later). After receiving the anonymized data for diagnosis, the diagnosis server performs image diagnosis using the equipped AI on the fundus image data included in the anonymized data for diagnosis. The diagnosis result is encrypted and sent to the intra-hospital server 300 and the terminal 400 via the administration server 100.

Examples of the diagnosis servers 201 to 203 are described below. Herein, the fundus image to be processed by each AI and the name of the disease being diagnosed are examples and various combinations of fundus images and diseases are possible.

The diagnosis server 201, which is an example of an image diagnosis device, is a diagnosis server equipped with an AI 221 configured to diagnose a diabetic retinopathy in a fundus image captured by the imaging device 500 having a narrow angle of view (angle of view of 30 to less than 100 with the center of the eyeball as the starting point), which is an example of a first angle of view. If the device information in the additional information is information indicating a narrow angle of view, the administration server 100 sends the anonymized data for diagnosis to the diagnosis server 201.

The diagnosis server 202 is a diagnosis server equipped with an AI 222 configured to diagnose a diabetic retinopathy in a fundus image captured by the imaging device 500 having a wide angle of view (angle of view of 100 to less than 200 with the center of the eyeball as the starting point), or a super-wide angle of view (angle of view of 200 or higher with the center of the eyeball as the starting point), which are both examples of a second angle of view. If the device information in the additional information is information indicating a wide angle of view and the diagnosis mode is information indicating a diabetic retinopathy, the administration server 100 sends the anonymized data for diagnosis to the diagnosis server 202.

The diagnosis server 203 is a diagnosis server equipped with an AI 223 that can diagnose not just a diabetic retinopathy but also a variety of fundus diseases in a fundus image captured by the imaging device 500 having a super-wide angle of view (angle of view of 200 or higher with the center of the eyeball as the starting point). If the device information in the additional information indicates a super-wide angle of view and the facility information indicates an ophthalmologist, the administration server 100 sends the anonymized data for diagnosis to the diagnosis server 203.

Figure 2:
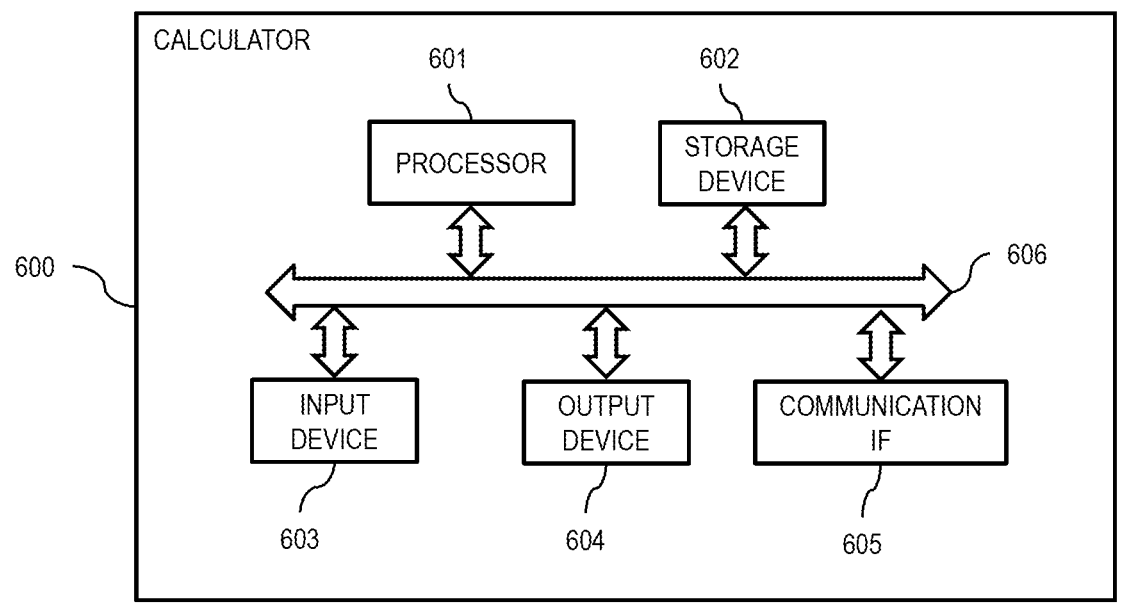
FIG. 2 is a block diagram illustrating hardware configuration examples of computers according to the first embodiment.

FIG. 2 is a block diagram illustrating hardware configuration examples of computers constituting the administration server 100, the diagnosis servers, the intra-hospital server 300, and the terminal 400. A computer 600 includes, for example, a processor (CPU) 601, a storage device 602, an input device 603, an output device 604, and a communication interface (IF) 605. These components are connected to each other via internal signal wiring 606.

The processor 601 executes a program stored in the storage device 602. The storage device 602 includes a memory. This memory incudes a ROM as a non-volatile storage element and a RAM as a volatile storage element. The ROM stores firmware (e.g., a BIOS). The RAM is a high-speed and volatile storage element such as a dynamic random-access memory (DRAM) and temporarily stores programs executed by the processor 601 and data used when executing the programs.

The storage device 602 includes an auxiliary storage device. This auxiliary storage device is a large-capacity and non-volatile storage device such as a magnetic storage device (HDD) or a flash memory (SSD), and stores programs executed by the processor 601 and data used when executing the programs. More specifically, the programs are read out from the auxiliary storage device, loaded to the memory and executed by the processor 601.

The input device 603 is an interface such as a keyboard or mouse that receives input from an operator. The output device 604 is a device such as a display or a printer that outputs an execution result of the program in a format recognizable by the operator. The input device 603 and the output device 604 may be formed integrally, such as in a touch-panel device. The communication I/F 605 is a network interface device that controls communication with other devices according to predetermined protocols.

The program to be executed by the processor 601 is provided to the computer 600 via a removable medium (CD-ROM, flash memory, etc.) or a network and stored in the non-volatile auxiliary storage device, which is an example of a permanent storage medium. Thus, the computer 600 preferably includes an interface configured to read data from a removable medium.

The administration server 100, the diagnosis server, the intra-hospital server 300, and the terminal 400 are all computer systems physically configured on one computer 600 or theoretically or physically configured on a plurality of computers 600, and may operate on separate threads on the same computer 600 or operate on a virtual computer built on a plurality of physical computer resources.

Figure 3:
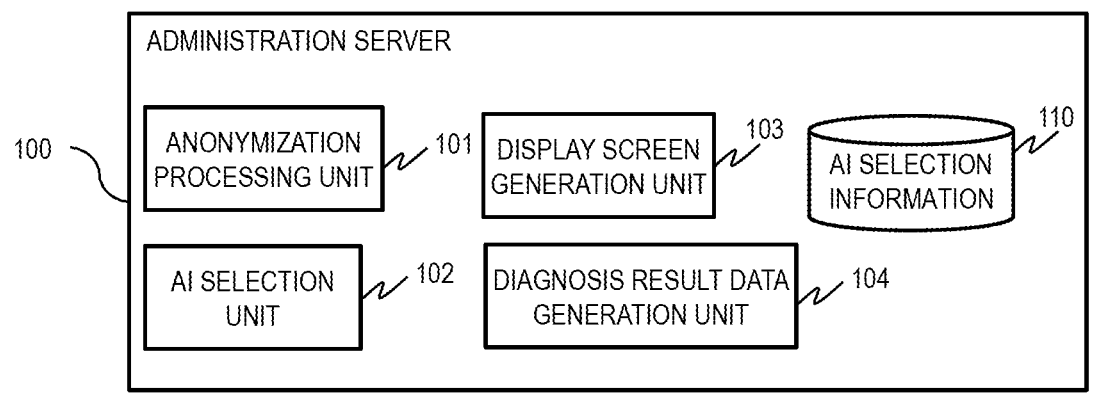
FIG. 3 is a block diagram illustrating a functional configuration example of an administration server according to the first embodiment.

FIG. 3 is a block diagram illustrating a functional configuration example of the administration server 100. The administration server 100 includes an anonymization processing unit 101, an AI selection unit 102, a display screen generation unit 103, and a diagnosis result data generation unit 104. The anonymization processing unit 101 anonymizes the patient information included in the data for diagnosis sent from the intra-hospital server 300. The AI selection unit 102 selects an AI for performing image diagnosis on the fundus image data included in the data for diagnosis based on the additional information included in the data for diagnosis.

The display screen generation unit 103 generates screen information displayed on the output device 604. The diagnosis result data generation unit 104 decrypts the encrypted diagnosis result received from the diagnosis server, generates a display screen (FIGS. 12, 13 and 14) displaying the diagnosis result and sends information on this display screen to the intra-hospital server 300.

The functional units in the administration server 100 are realized by a processor 601 in the computer 600 configured to operate the administration server 100. Specifically, the processor 601 operates according to an anonymization processing program stored in a memory in the storage device 602 to function as the anonymization processing unit 101, and operates according to an AI selection program stored in a memory in the storage device 602, to function as the AI selection unit 102. The same applies to other functional units in the administration server 100 and other devices, where the processor 601 operates according to programs loaded into memories.

The administration server 100 holds AI selection information 110. The AI selection information 110 holds corresponding information between the additional information and the diagnosis server 201, the diagnosis server 202, and the diagnosis server 203. As described below, the AI 221, the AI 222 and the AI 223 include different image diagnosis models. Thus, the AI selection information 110 includes corresponding information between the additional information and the image diagnosis models. The AI selection information 110 is written with conditional branches based on the values of one or more types of additional information. Thus, the AI corresponding to the additional information is preset. The AI selection information 110 is also written with a table of correspondence between values (or value ranges) of one or more types of additional information and the AI 220.

The AI selection information 110 is stored in an auxiliary storage device included in the storage device 602 of the computer 600 that realizes the administration server 100. The same applies to information and databases stored in other devices, where the information and databases are stored in an auxiliary storage device included in the storage device 602 of the computer 600 that realizes the other device.

In the present embodiment, information used by each device included in the image diagnosis system may be represented by any data structure regardless of the data structure. For example, a data structure appropriately selected from a table, a list, a database or a queue may store the information. Each type of information is stored and held in a non-volatile memory, for example.

Figure 4:
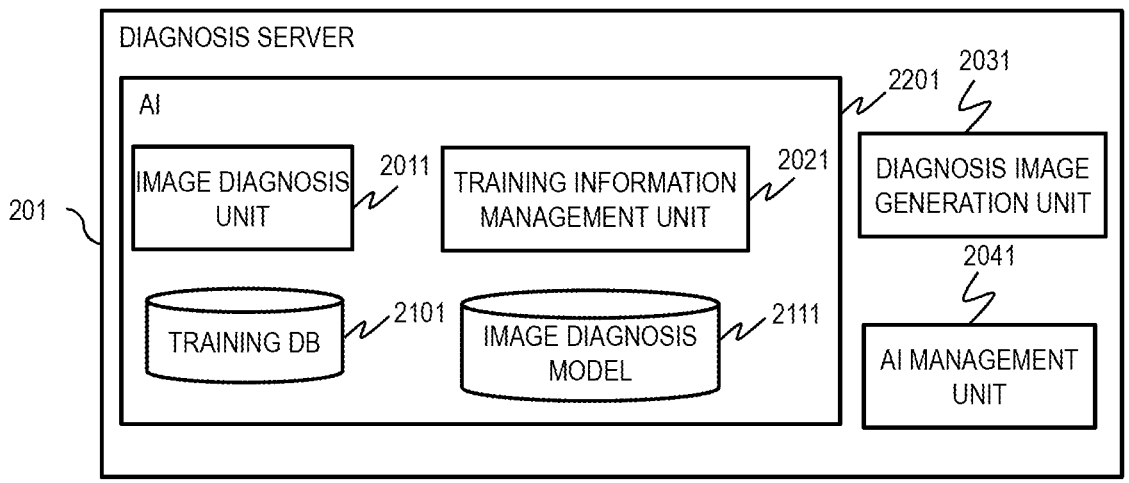
FIG. 4 is a block diagram illustrating a functional configuration example of a diagnosis server according to the first embodiment.

FIG. 4 is a block diagram illustrating a functional configuration example of the diagnosis server 201. The functional configuration of the diagnosis server 201, the diagnosis server 202, and the diagnosis server 203 are only different in terms of the AI functions (the display screen generation unit, the administration unit and other units have the same functions). Thus, the functional configuration of the diagnosis server 201 will be described.

The diagnosis server 201 includes, for example, an image diagnosis unit 2011, a training information management unit 2021, a diagnosis image generation unit 2031, and a management unit 2041. The diagnosis server 201 holds a training DB 2101 and an image diagnosis model 2111. The training DB 2101 is a database used for building the image diagnosis model 2111. The image diagnosis model 2111 is a model that outputs a diagnosis result when image data is input. The image diagnosis model 2111 outputs a symptom grade of diabetic retinopathy in the fundus image captured by the imaging device 500 having a narrow angle of view (angle of view of 30 to less than 100 with the center of the eyeball as the starting point) as the diagnosis result. In the present embodiment, the symptom grading of diabetic retinopathy is the International Clinical Diabetic Retinopathy Disease Severity Scale classified into five grades.

The image diagnosis unit 2011, the training information management unit 2021, the training DB 2101, and the image diagnosis model 2111 are realized by the AI 221. The image diagnosis unit 2011 performs image analysis using the image diagnosis model 2111 on the fundus image data included in the anonymized data for diagnosis received from the administration server 100.

The training information management unit 2021 stores the patient eye image data and the image diagnosis result included in the anonymized data for diagnosis in the training DB 210 as training data for AI to update the training DB 210. The training information management unit 2021 updates (e.g., optimizes) the image diagnosis model 2111 through training based on the updated training DB 2101.

The diagnosis image generation unit 2031 generates a diagnosed fundus image in which information including a mark indicating the location of an abnormality and the letters of a name of a disease are superimposed on the fundus image subject to diagnosis. The management unit 2041 manages the AI 221. The diagnosed fundus image is sent to the administration server 100 together with the diagnosis result.

The diagnosis server 201 may or may not include a training function for the image diagnosis model 2111. In other words, the diagnosis server 201 may continue to perform image diagnosis with a preset and fixed image diagnosis model 2111 without updating the image diagnosis model 2111. In this case, the diagnosis server 201 may or may not include the training information management unit 2021 and the training DB 2101.

The diagnosis server 202 and the diagnosis server 203 have the same configuration as the diagnosis server 201 except that the diagnosis server 202 and the diagnosis server 203 have different image diagnosis models.

The image diagnosis model held by the diagnosis server 202 is a model that outputs a diagnosis result when image data is input and outputs a symptom grade of diabetic retinopathy in the fundus image captured by the imaging device 500 having a wide angle of view (angle of view of 100 to less than 200 with the center of the eyeball as the starting point) or a super-wide angle of view (angle of view of 200 or higher with the center of the eyeball as the starting point) as the diagnosis result.

The image diagnosis model held by the diagnosis server 203 is a model that outputs a diagnosis result when image data is input and outputs not just a diagnosis result of diabetic retinopathy, but diagnosis results of various fundus diseases in the fundus image captured by the imaging device 500 having a super-wide angle of view (angle of view of 200 or higher with the center of the eyeball as the starting point).

The image diagnosis unit, training information management unit and learning DB in the diagnosis server 202 and diagnosis server 203 are compatible with the image diagnosis models held in those servers.

Figure 5:
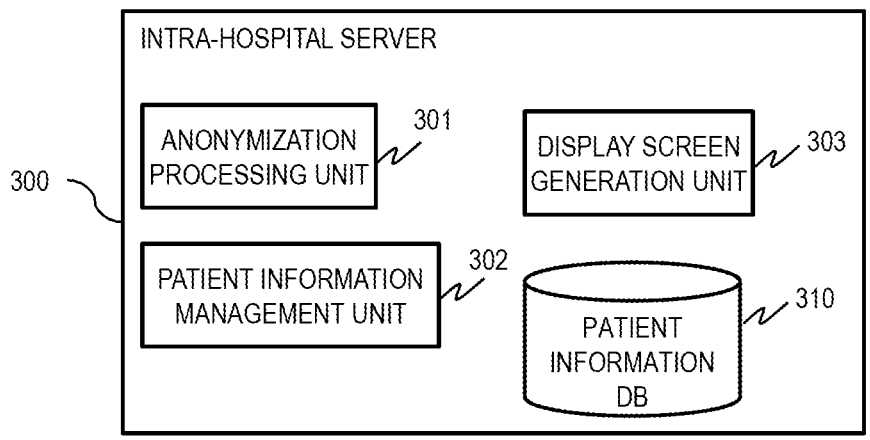
FIG. 5 is a block diagram illustrating a functional configuration example of an intra-hospital server according to the first embodiment.

FIG. 5 is a block diagram illustrating a functional configuration example of the intra-hospital server 300. The intra-hospital server 300 includes, for example, the anonymization processing unit 301, the patient information management unit 302, and the display screen generation unit 303. The intra-hospital server 300 holds a patient information DB 310.

The anonymization processing unit 301 anonymizes the patient information included in the data for diagnosis. The patient information management unit 302 stores the patient information included in the data for diagnosis in the patient information DB 310, acquires the patient information from the patient information DB 310 and adds it to the data for diagnosis. The display screen generation unit 303 generates screen information to be displayed on the output device 604. The patient information DB 310 holds patient information.

Figure 6:
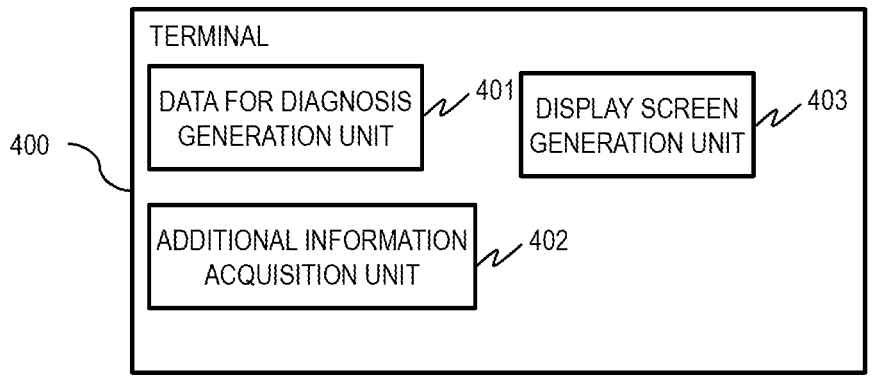
FIG. 6 is a block diagram illustrating a functional configuration example of a terminal according to the first embodiment.

FIG. 6 is a block diagram illustrating a functional configuration example of the terminal 400. The terminal 400 includes a data for diagnosis generation unit 401, an additional information acquisition unit 402, and a display screen generation unit 403. The data for diagnosis generation unit 401 generates the data for diagnosis including the patient information, the additional information, and the patient eye image data. The additional information acquisition unit 402 acquires additional information used for selecting an AI (or a diagnosis server including an appropriate AI for diagnosis). The display screen generation unit 403 generates screen information to be displayed on the output device 604.

Figure 7:
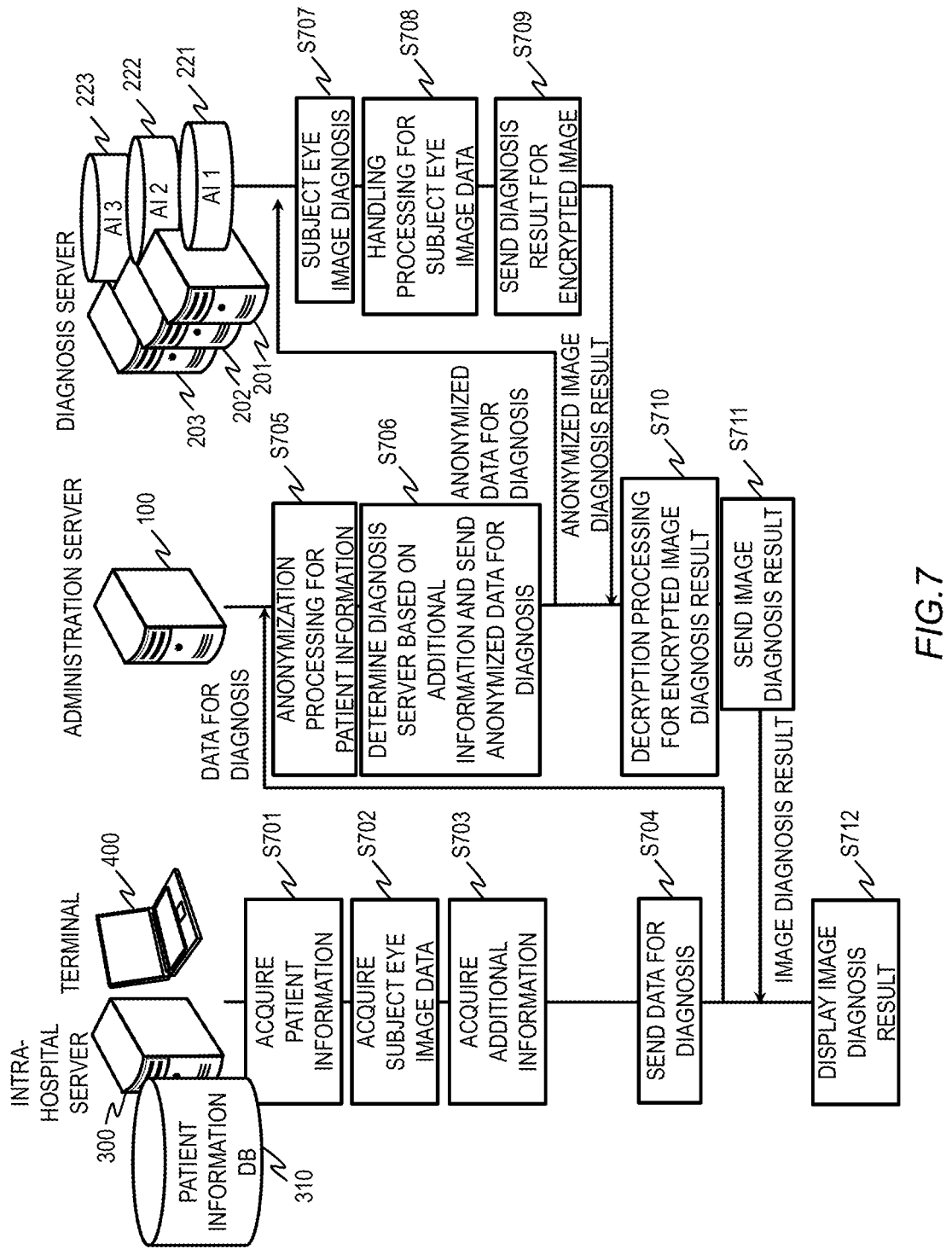
FIG. 7 is a sequence diagram illustrating image diagnosis processing of the image diagnosis system according to the first embodiment.

FIG. 7 is a sequence diagram illustrating image diagnosis processing of the image diagnosis system according to the first embodiment. In the example of FIG. 7, a diagnosis server to perform image diagnosis on a fundus image is selected based on information such as device information of the imaging device 500.

First, the data for diagnosis generation unit 401 of the terminal 400 receives input of patient information via the input device 603 (S701). An ID that identifies the patient and information such as the age, sex, address, medical history, medication history and examination results are all examples of patient information. For a patient for which information is already registered in the patient information DB 310, if the ID that identifies the patient is input, other patient information does not need to be input.

The data for diagnosis generation unit 401 acquires fundus image data for both eyes of the patient sent from the imaging device 500 (S702). In the present embodiment, the fundus image data for both eyes may be acquired or fundus image data for either the left eye or the right eye may be acquired. The data for diagnosis generation unit 401 generates a left/right eye flag indicating whether the fundus image data is data for both eyes, data for only the right eye, or data for only the left eye. The data for diagnosis generation unit 401 may acquire fundus image data from a device other than the imaging device 500.

Then, the additional information acquisition unit 402 acquires the additional information (S703). Specifically, for example, the additional information acquisition unit 402 acquires device information from the imaging device 500 or receives input about the hospital in which the terminal 400 is used or the department of the physician as the additional information.

The additional information may be stored in advance in the storage device 602 of the terminal 400. For example, the imaging device 500 may embed the device information in the fundus image data as metadata and the additional information acquisition unit 402 may acquire the device information from the fundus image data.

Next, the data for diagnosis generation unit 401 sends the data for diagnosis including the patient information, the fundus image data, the left/right eye flag, and the additional information to the administration server 100 via the intra-hospital server 300 (S704). The patient information management unit 302 of the intra-hospital server 300 stores the patient information received from the terminal 400 in the patient information DB 310.

If the patient information received from the terminal 400 is insufficient, the patient information management unit 302 may reference the patient information DB 310 to acquire patient information and supplement the patient information. Specifically, if, for example, the patient information received from the terminal 400 is only the ID that identifies the patient, the patient information management unit 302 acquires patient information corresponding to the ID from the patient information DB 310 and sends data for diagnosis including the acquired patient information to the administration server 100.

Then, the anonymization processing unit 101 of the administration server 100 performs anonymization processing using a predetermined algorithm on the patient information included in the received data for diagnosis (S705). The anonymization processing is processing of anonymizing the patient ID (replacing the patient ID with an ID unique to the fundus image data) and deleting personal information of the patient, such as their name and the name of disease. The anonymization processing unit 101 may anonymize only part of the patient information (for example, sensitive information related to privacy). The anonymization processing for the patient information may be performed in advance by, for example, the anonymization processing unit 301 of the intra-hospital server 300 before the data for diagnosis is sent to the administration server 100.

The AI selection unit 102 of the administration server 100 selects at least one of the diagnosis server 201, the diagnosis server 202, and the diagnosis server 203 based on the AI selection information 110 and the additional information included in the received data for diagnosis and sends the anonymized data for diagnosis including the anonymized patient information, the fundus image data, the left/right eye flag, and the additional information (see FIG. 11 described later) to the selected diagnosis server (in this embodiment, the diagnosis server 201 is selected) (S706). Step S706 will be described in detail later.

The AI selection unit 102 may encrypt the anonymized data for diagnosis using an encryption key and send the encrypted data for diagnosis to the selected diagnosis server 201. In this case, the diagnosis server 201 includes a decryption key corresponding to the above-described encryption key and decrypts the anonymized data for diagnosis with the encryption key in Step S707 to be described later.

Then, the image diagnosis unit 2011 of the diagnosis server 201 that has received the anonymized data for diagnosis performs image diagnosis on the fundus image data included in the received anonymized data for diagnosis by using the image diagnosis model 2111 that diagnoses a diabetic retinopathy in a fundus image with a narrow angle of view (S707).

The training information management unit 2021 of the diagnosis server 201 updates the training DB 2101 by storing the fundus image data in the training DB 2101 as training data and updates the image diagnosis model 2111 based on the updated training DB 2101 (S708). The training information management unit 2021 may store both the anonymized patient information and the additional information in the training DB 2101 as training data.

Then, the management unit 2041 generates image diagnosis result data including at least the anonymized patient information and an image diagnosis result. The management unit 2041 uses the encryption key held in the diagnosis server 201 to encrypt the image diagnosis result and generate an encrypted image diagnosis result. Then, the management unit 2041 sends the encrypted image diagnosis result to the administration server 100 (S709). The image diagnosis result data may include a diagnosed fundus image in which a mark indicating the location of an abnormality and the letters of the name of a disease are superimposed on the fundus image subject to diagnosis.

Then, the diagnosis result data generation unit 104 of the administration server 100 decrypts the received encrypted image diagnosis result using the encryption key held in the administration server 100 (S710). The diagnosis result data generation unit 104 also restores the anonymized patient information. The decrypted image diagnosis result is associated with the patient information related to the patient before anonymization.

Next, the diagnosis result data generation unit 104 generates a display screen (FIG. 12) indicating a diagnosis result including a grade of diabetic retinopathy as a diagnosis result, assigns a patient ID, and stores the display screen in a memory (not shown).

If the administration server 100 receives the encrypted image diagnosis result from the diagnosis server 202, the diagnosis result data generation unit 104 generates a display screen (FIG. 13) indicating a diagnosis result. If the administration server 100 receives the encrypted image diagnosis result from the diagnosis server 203, the diagnosis result data generation unit 104 generates a display screen (FIG. 14) indicating a diagnosis result.

Then, the diagnosis result data generation unit 104 associates the display screen indicating a diagnosis result with the patient information and sends this information to the intra-hospital server 300 (S711). The display screen generation unit 303 of the intra-hospital server 300 displays a display screen based on the received display screen indicating a diagnosis result and the patient information on the output device 604 of the intra-hospital server 300 (S712). The terminal 400 may acquire the image diagnosis result and the patient information from the intra-hospital server 300 and the display screen generation unit 403 of the terminal 400 may display the display screen based on the display screen indicating a diagnosis result and the patient information on the output device 604 of the terminal 400.

Further, the display screen generation unit 103 of the administration server 100 may generate information for the display screen based on the image diagnosis result and the patient information and send that information to the intra-hospital server 300, and the intra-hospital server 300 and the terminal 400 may display the display screen according to the generated information.

Figure 8:
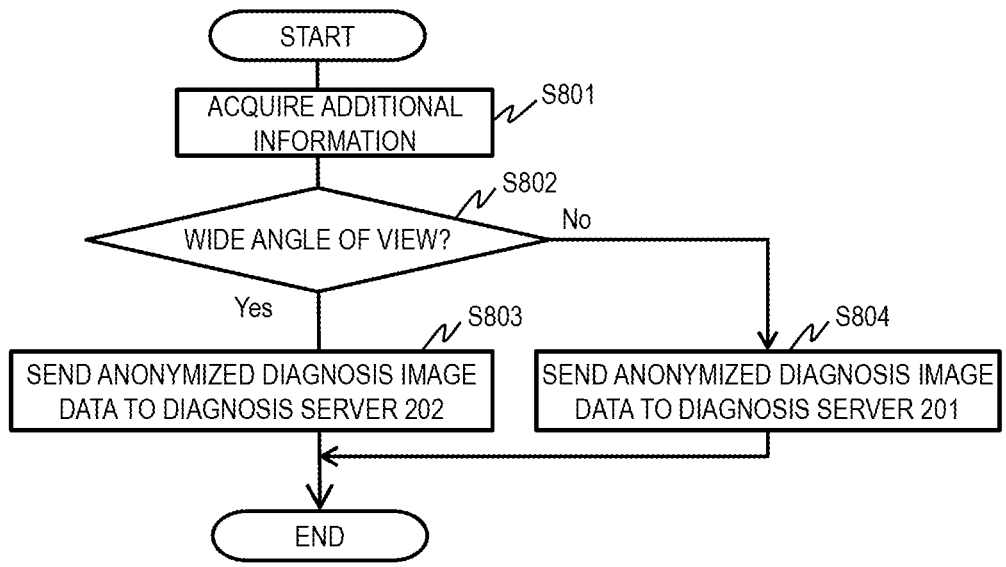
FIG. 8 is a flowchart illustrating an example of diagnosis server determination processing according to the first embodiment.

FIG. 8 is a flowchart illustrating an example of diagnosis server determination processing in Step S706. In the example of FIG. 8, the diagnosis server that sends the anonymized data for diagnosis is determined based on angle-of-view information included in the additional information. First, the AI selection unit 102 of the administration server 100 acquires additional information including the angle-of-view information from the data for diagnosis (S801).

The AI selection unit 102 determines whether the angle of view in the angle-of-view information is a wide angle of view (S802). Specifically, if the angle-of-view information indicates a specific angle, the angle of view is determined to be a wide angle of view if the angle is more than or equal to a predetermined value (e.g., 100°) and determined to not be a wide angle of view (a narrow angle of view) if less than the predetermined value.

For example, the administration server 100 may hold the device information for each imaging device 500. Specifically, the device information is a look-up table associating and defining the model and terminal ID of each imaging device 500, the angle of view, the resolution, and other information. In this case, the AI selection unit 102 acquires the model or terminal ID of the imaging device 500 from the additional information, refers to the device information, and determines whether the angle of view of the imaging device 500 indicated by the model number or terminal ID is a wide angle of view.

If it is determined that the angle of view indicated by the angle-of-view information is a wide angle of view (S802: Yes), the AI selection unit 102 sends the anonymized data for diagnosis to the diagnosis server 202 (S803) and, if it is determined that the angle of view is not a wide angle of view (S802: No), the AI selection unit 102 sends the anonymized data for diagnosis to the diagnosis server 201 (S804) and the processing in Step S705 ends.

In FIG. 8, the AI in the diagnosis server 202 can perform high-precision image diagnosis on the fundus image captured at a wide angle of view, and the AI in the diagnosis server 201 can perform high-precision image diagnosis on the subject eye image captured at a narrow angle of view. As a result, the AI selection unit 102 can select the appropriate diagnosis server according to the imaging angle of view of the subject eye image.

In FIG. 8, the AI selection unit 102 determines whether the angle of view indicated by the angle-of-view information is a wide angle of view and selects either the diagnosis server 201 or the diagnosis server 202 as the diagnosis server to which to send information. Alternatively, the AI selection unit 102 may determine whether the angle of view indicated by the angle-of-view information corresponds to one classification among three or more angle of view classifications, refer to the AI selection information 110 and select the diagnosis server corresponding to the classification.

In FIG. 8, the diagnosis server is selected according to the angle of view, but the diagnosis server may be selected by using another element included in the additional information. For example, the AI selection unit 102 may determine the diagnosis server by using the facility information (physician using the terminal 400, name of hospital, installation location of terminal 400 (information related to department, e.g., ophthalmology, internal medicine or diabetic tract medicine, or information related to facility, e.g., optical retailer or diagnostic facility), or prices of diagnostic plans at the hospital or clinic in which the terminal 400 is installed, etc.) included in the additional information.

At this time, the AI selection unit 102 selects the diagnosis server 203 if the department information indicates ophthalmology and selects the diagnosis server 201 if the department information indicates internal medicine. Further, the AI selection unit 102 selects the diagnosis server 202 or the diagnosis server 203 if the price of the diagnostic plan is more than or equal to a predetermined value and selects the diagnosis server 201 if the price of the diagnostic plan is less than the predetermined value.

It is assumed that the diagnosis server 201 equipped with the AI that diagnoses the onset of a particular disease (e.g., diabetic retinopathy) with high precision and the diagnosis server 203 that comprehensively diagnoses the onset of a plurality of different diseases are present. It is also assumed that the additional information includes information indicating diseases to be diagnosed. In this case, the AI selection unit 102 selects the diagnosis server 201 if the disease to be diagnosed indicated by the additional information is the particular disease and selects the diagnosis server 203 if the disease to be diagnosed indicated by the additional information is not the particular disease and a comprehensive diagnosis is required.

For example, it is assumed that the diagnosis server 201 equipped with the AI that performs high-precision image diagnosis on the subject eye image captured by a fundus camera and the diagnosis server 202 equipped with the AI that performs high-precision image diagnosis on the subject eye image captured by a scanning laser ophthalmoscope are present. It is also assumed that the additional information includes information indicating modality. In this case, the AI selection unit 102 selects the diagnosis server 201 if the modality indicated by the additional information is the fundus camera and selects the diagnosis server 202 if the modality indicated by the additional information is the scanning laser ophthalmoscope.

As such, the AI selection unit 102 can select the diagnosis server equipped with the most appropriate AI from the plurality of diagnosis servers, based on the additional information. With this configuration, the user need not worry about which diagnosis server to select and the fundus image data can be sent to the appropriate diagnosis server.

Figure 9:
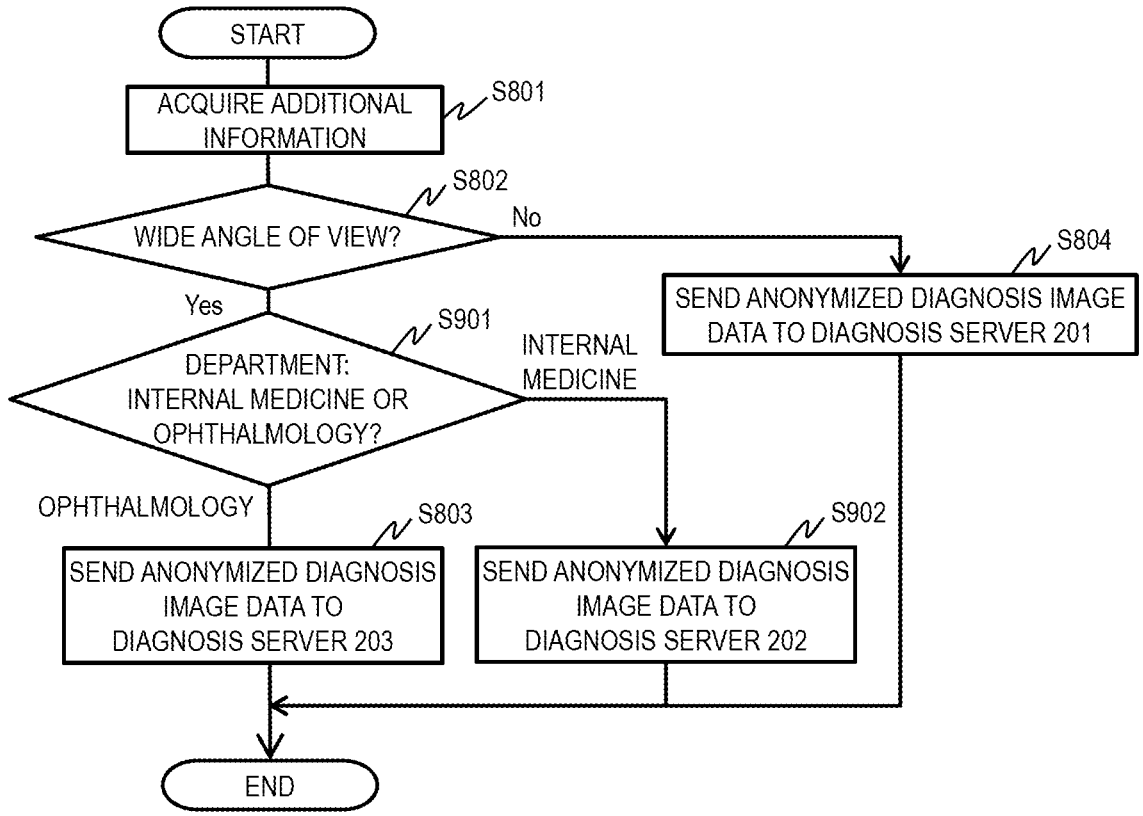
FIG. 9 is a flowchart illustrating another example of the diagnosis server determination processing according to the first embodiment.

FIG. 9 is a flowchart illustrating another example of the diagnosis server determination processing in Step S706. In FIG. 9, the diagnosis server to which the anonymized data for diagnosis is sent is determined based on a plurality of different types of information (angle-of-view information and department information) included in the additional information. In other words, it is assumed that the angle-of-view information and the department information are included in the additional information. Differences to FIG. 8 will be described.

If it is determined that the angle of view indicated by the angle-of-view information is a wide angle of view (S802: Yes), the AI selection unit 102 determines whether the department indicated by the department information is ophthalmology or internal medicine (S901). If it is determined that the department indicated by the department information is ophthalmology (S901: Ophthalmology), the AI selection unit 102 sends the anonymized data for diagnosis to the diagnosis server 203 (S803) and, if it is determined that the department indicated by the department information is internal medicine (S901: Internal medicine), the AI selection unit 102 sends the anonymized data for diagnosis to the diagnosis server 202 (S902) and the processing in Step S705 ends.

In FIG. 9, the AI in the diagnosis server 202 can perform high-precision and detailed diagnosis including the symptom level of a particular disease (e.g., diabetic retinopathy) on the fundus image data captured at a wide angle of view. The AI in the diagnosis server 201 can perform high-precision image diagnosis on the fundus image data captured at a narrow angle of view. Further, the AI in the diagnosis server 203 can diagnose the onset of a plurality of different diseases with high precision in the fundus image data captured at a wide angle of view.

As a result, the AI selection unit 102 can select the appropriate diagnosis server according to the imaging angle of view of the subject eye image and the hospital in which the terminal 400 is installed or the department of the physician using the terminal 400. In other words, the fundus image data can be sent to the appropriate diagnosis server based on the plurality of different types of information (angle-of-view information and department information) included in the additional information.

In FIG. 9, all fundus image data captured at a narrow angle of view is sent to the diagnosis server 201, but the same may apply to the subject eye image data captured at a narrow angle of view. Further conditional branches based on the additional information may be added and a diagnosis server to which to the subject eye image data is sent may be selected from a plurality of different diagnosis servers.

In FIG. 9, one particular diagnosis server is selected from a plurality of diagnosis servers by using two types of additional information, but the correspondence between the additional information and the diagnosis servers may be set as desired according to the characteristics of the AI in the respective diagnosis servers. For example, three or more types of additional information may be used, and the diagnosis server may be determined based on any conditional branches by using a plurality of types of additional information.

Figure 10:
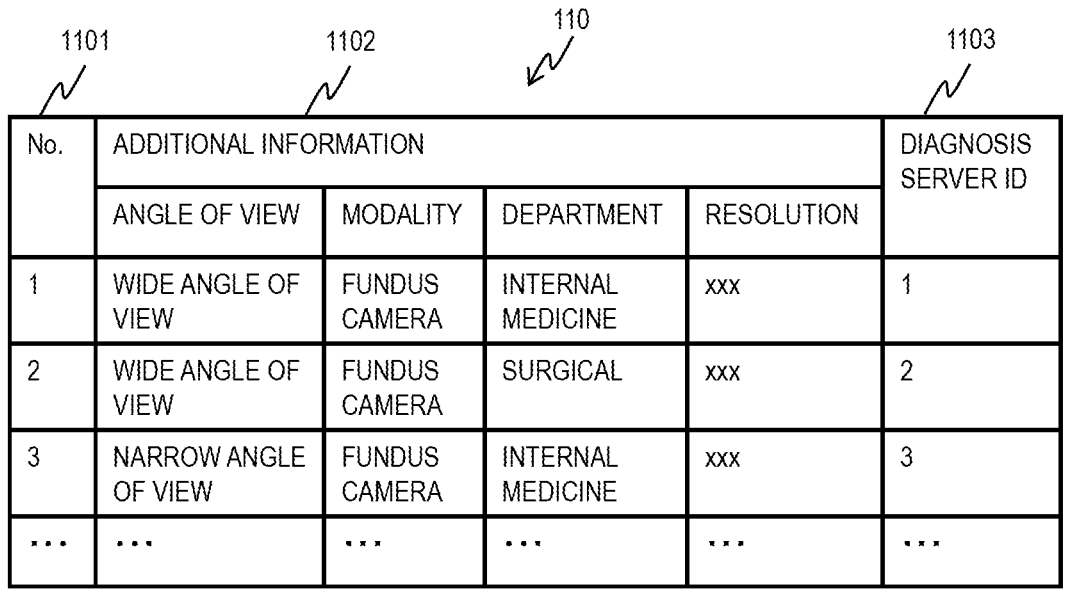
FIG. 10 illustrates an example of the AI selection information according to the first embodiment.

FIG. 10 illustrates an example of the AI selection information 110. In the example of FIG. 10, correspondence between the additional information and each diagnosis server is expressed as a table. The AI selection information 110 includes, for example, a record number column 1101, an additional information column 1102, and a diagnosis server ID column 1103. The record number column 1101 holds numbers that identify records of the AI selection information 110. The additional information column 1102 holds elements (angle-of-view information, modality information, department information, resolution information, etc.) of one or more types of additional information. The diagnosis server ID column 1103 holds IDs that identify the diagnosis server to which the anonymized data for diagnosis corresponding to a combination of the additional information is sent.

For example, the AI selection unit 102 acquires the additional information in Step S706 and sends the anonymized data for diagnosis to a diagnosis server including a diagnosis server ID corresponding to the acquired additional information in the table of FIG. 10. Note that the conditional branches in FIGS. 8 and 9 may be expressed in a table as in FIG. 10.

Figure 11:
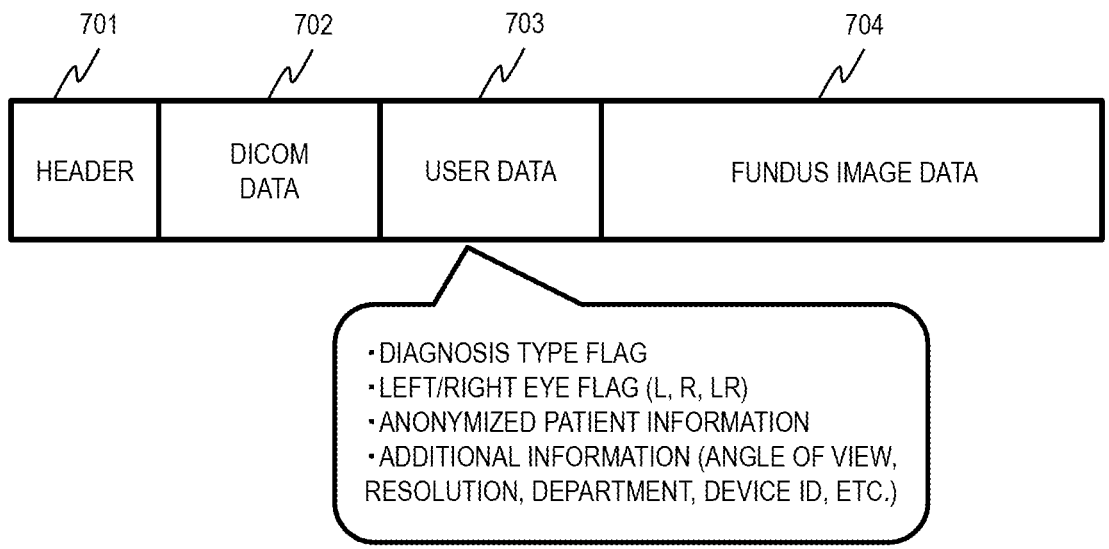
FIG. 11 illustrates an example of a data structure of anonymized data for diagnosis according to the first embodiment.

FIG. 11 illustrates an example of a data structure of the anonymized data for diagnosis sent from the administration server 100 to the diagnosis server. The anonymized data for diagnosis includes, for example, a header 701, digital imaging and communications in medicine (DICOM) data 702, user data 703, and fundus image data 704.

The header 701 includes information such as origin and destination of the data and the type of data (data types such as medical image, document, e-mail, etc.). The DICOM data 702 includes, for example, the format of the medical image captured by the imaging device 500 and information defining communication protocols between medical devices including the imaging device 500.

The user data 703 includes, for example, a diagnosis type flag, the left/right eye flag, the anonymized patient information, and the additional information. The diagnosis type flag is a flag indicating the disease name (value identifying diabetic retinopathy, age-related macular degeneration and all fundus diseases) diagnosed by the diagnosis server selected by the AI selection unit 102. The left/right eye flag is a flag indicating whether the fundus image data 704 is image data for the right eye, image data for the left eye, or image data for both eyes (e.g., one value among L, R and LR). Among the additional information, information that can also be written in the DICOM data 702, such as the terminal ID of the imaging device 500 and the modality, may only be written in the DICOM data 702.

Figure 12:
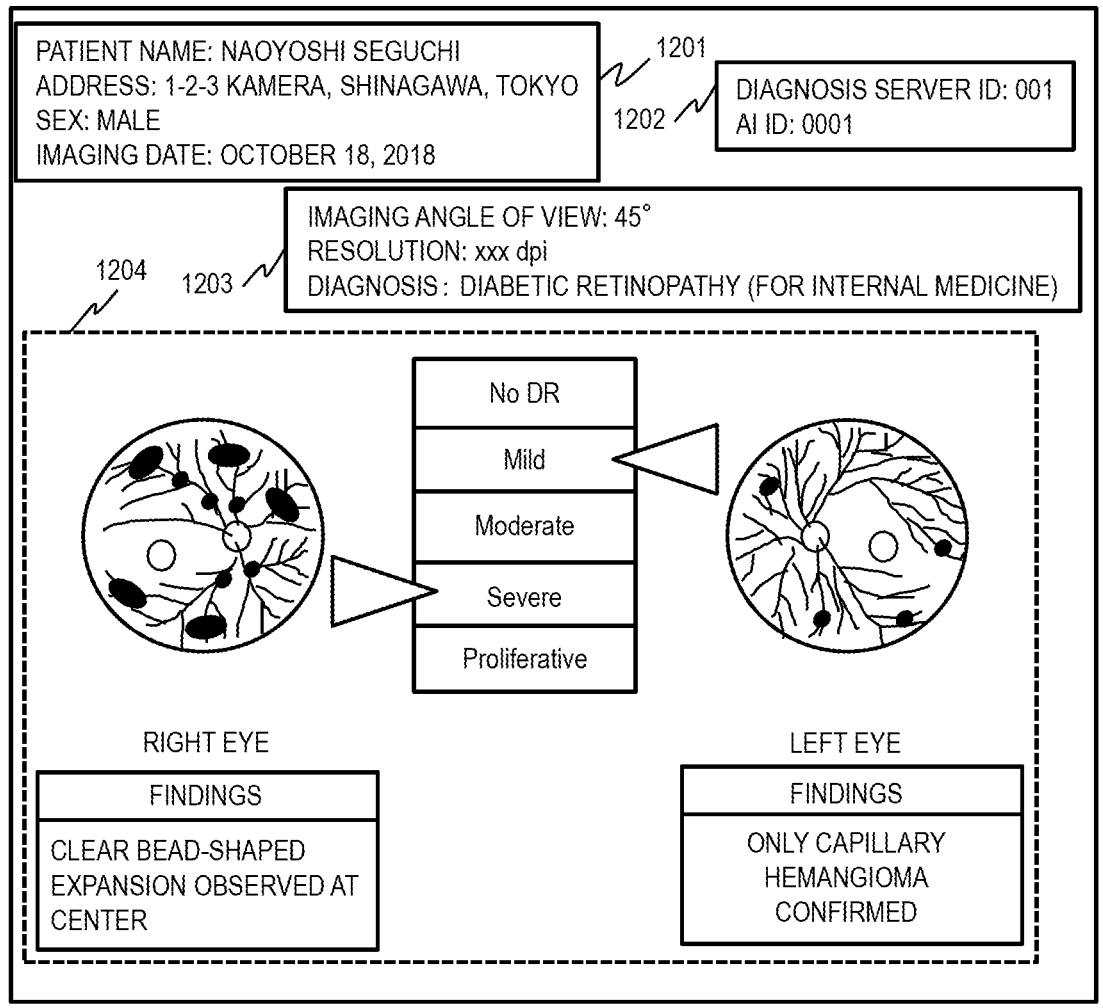
FIG. 12 illustrates an example of a display screen that displays a diagnosis result according to the first embodiment.

FIG. 12 illustrates an example of a display screen that displays a diagnosis result determined by the diagnosis server 201. FIG. 12 is a display screen (screen layout) in a case where a symptom level diagnosis for diabetic retinopathy is performed on subject eye image (fundus image) data captured at a narrow angle of view.

The display screen includes a patient information display area 1201, an AI information display area 1202, an additional information display area 1203, and a diagnosis result display area 1204. In the patient information display area 1201, for example, patient information included in image diagnosis data is displayed. In the AI information display area 1202, an ID of the diagnosis server that performed image diagnosis and an ID (or version number) of the AI that performed image diagnosis is displayed. In the additional information display area 1203, some (angle of view, resolution, diagnosis type, etc.) or all of the additional information included in the data for diagnosis is displayed.

In the diagnosis result display area 1204, information indicating the diagnosis result of fundus image data determined by the diagnosis server is displayed. In the example of FIG. 12, fundus images for both eyes, a bar indicating the symptom level among five levels for diabetic retinopathy in both eyes, and findings in both eyes are displayed in the diagnosis result display area 1204.

In the example of FIG. 12, an image of the right eye and a right-facing arrow (indicator) indicating the symptom level of diabetic retinopathy in the image of the right eye are displayed to the right of the bar, and an image of the left eye and a left-facing arrow indicating the symptom level of diabetic retinopathy in the image of the left eye are displayed to the left of the bar. With this configuration, the user is able to understand the symptom level for diabetic retinopathy in both eyes and the differences between symptom levels by simply looking at the diagnosis result display area 1204. Further, findings in the diagnosis result display area 1204 are generated by the AI in the diagnosis server. These findings may be input or edited by the user using the terminal 400.

Figure 13:
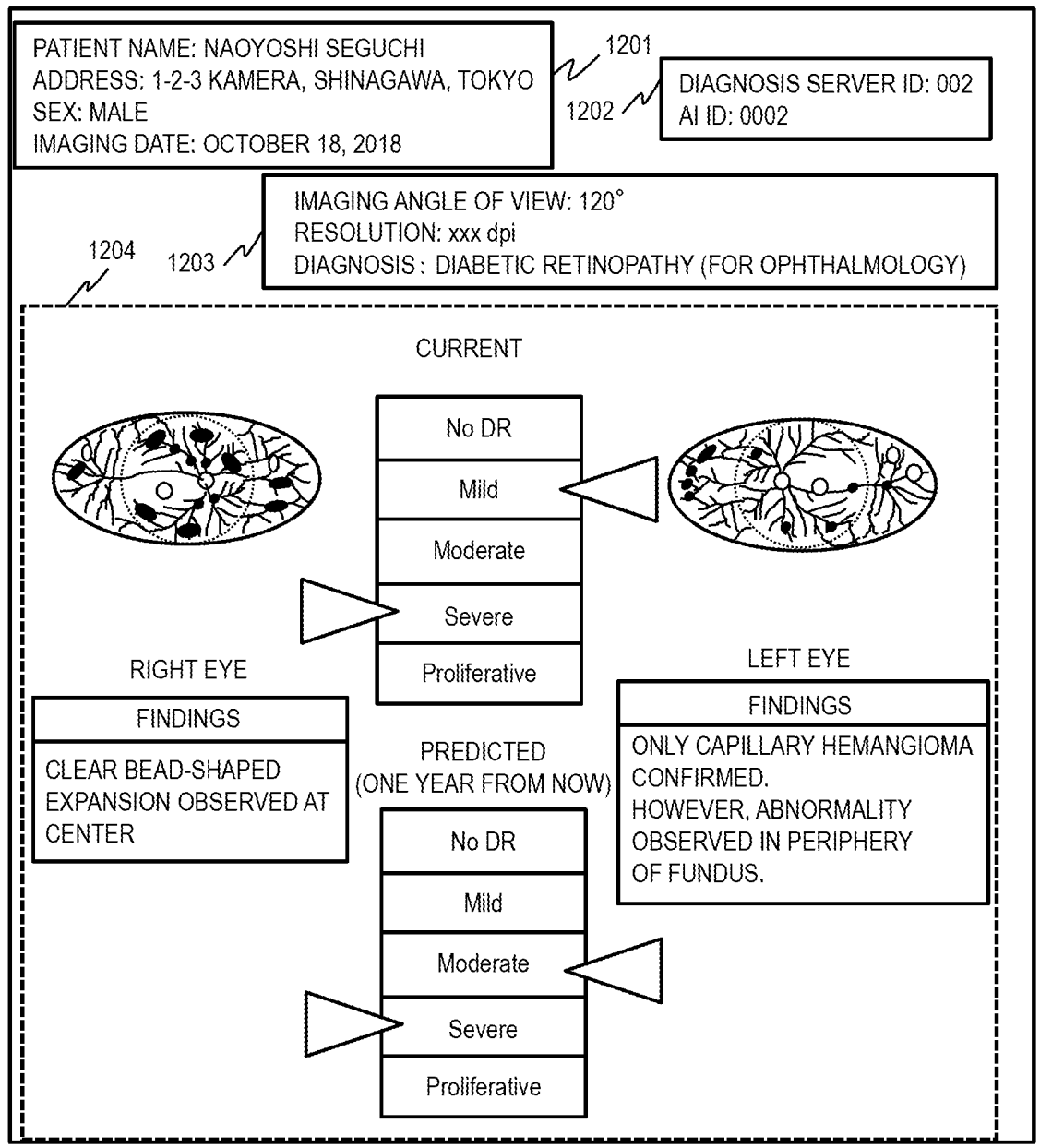
FIG. 13 illustrates an example of a display screen that displays a diagnosis result according to the first embodiment.

FIG. 13 illustrates an example of a display screen that displays a diagnosis result determined by the diagnosis server 202. FIG. 13 illustrates a display screen in a case where a diagnosis for the symptom level of diabetic retinopathy is performed on wide-angle fundus image data captured at a wide angle of view. When suffering from diabetic retinopathy, initial symptoms involve an abnormality occurring around the periphery of the fundus. Then, the abnormality spreads to the center of the eye. By imaging the fundus at a wide angle of view, wide-angle fundus image data including both the center and periphery of the fundus can be obtained. Thus, the AI that performs image diagnosis on the wide-angle fundus image captured at a wide angle of view not only estimates the symptom level of the current diabetic retinopathy, but also predicts a future symptom level in consideration of the state of the periphery of the fundus.

Thus, in the diagnosis result display area 1204 in the example of FIG. 13, a bar indicating the future symptom level of diabetic retinopathy in both eyes is displayed in addition to the bar indicating the current symptom level in five levels of the diabetic retinopathy in both eyes. Further, a future (in FIG. 13, this period is one year in the future but may be three months or six months in the future) predicted state is added to the findings in the diagnosis result display area 1204.

In the example of FIG. 13, the current symptom level and the future symptom level are displayed in the diagnosis result display area 1204, but the current symptom level at the center of the fundus and the current symptom level at the periphery may be displayed in the diagnosis result display area 1204.

Figure 14:
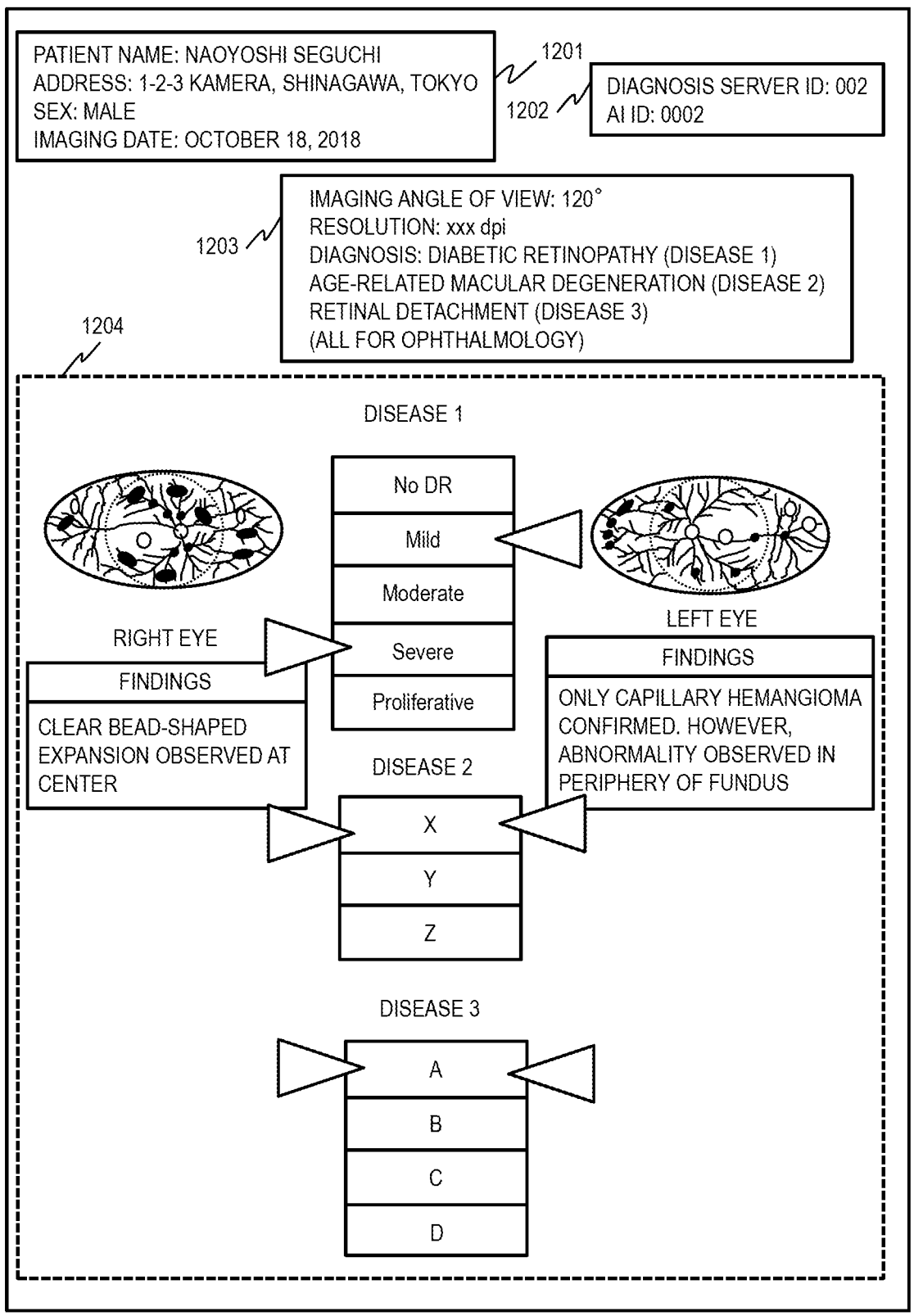
FIG. 14 illustrates an example of a display screen that displays a diagnosis result according to the first embodiment.

FIG. 14 is an illustration of an example of a display screen that displays a diagnosis result determined by the diagnosis server 203. FIG. 14 illustrates a display screen in a case where a plurality of diseases are diagnosed in wide-angle fundus image data captured at a wide angle of view. One of the plurality of diseases is diabetic retinopathy. This is the same as the display of the diagnosis result of diabetic retinopathy in FIG. 13. In FIG. 14, bars and arrows (indicators) indicating the categories and progression of symptoms for a disease 2 and a disease 3 are also displayed. The disease 2 and disease 3 are fundus diseases that can be identified by the AI 223 of the diagnosis server 203, such as age-related macular degeneration and detached retina.

A modification example of the display screen that displays the diagnosis result will now be explained.

If an image diagnosis is performed and the onset of a disease can be diagnosed but the symptom level of the disease cannot be determined, information indicating the disease that is predicted to occur may be displayed in the diagnosis result display area 1204.

In such a case, a message recommending image diagnosis by a diagnosis server including an AI that can diagnose a specific symptom level of the disease that is predicted to occur may also be displayed in the diagnosis result display area 1204.

The administration server 100 may hold correspondence information between the disease and the diagnosis server equipped with the AI that can diagnose the symptom level of the disease. In this case, when the administration server 100 receives a command for performing image diagnosis according to the message from the intra-hospital server 300, the administration server 100 refers to the correspondence information to identify, from among the diagnosis servers that can send information, one diagnosis server equipped with an AI that can diagnose the symptom level of the disease. Then, the administration server 100 may send and display information indicating the diagnosis server to the intra-hospital server 300 and send the anonymized data for diagnosis to the diagnosis server again to request the image diagnosis.

The image diagnosis system includes the diagnosis server equipped with an AI (hereinafter, "AI A") that performs image diagnosis on an image with a low resolution (e.g., a first resolution less than a predetermined resolution), and a diagnosis server equipped with an AI (hereinafter, "AI B") that performs image diagnosis on an image with a high resolution (e.g., a second resolution more than or equal to the predetermined resolution). In this case, if the AI A diagnoses an abnormality in the fundus in the diagnosis result, a message recommending an image diagnosis by the AI B by using higher resolution fundus image data may be displayed in the diagnosis result display area 1204. Alternatively, a message recommending imaging with higher resolution fundus image data may be displayed.

Figure 15:
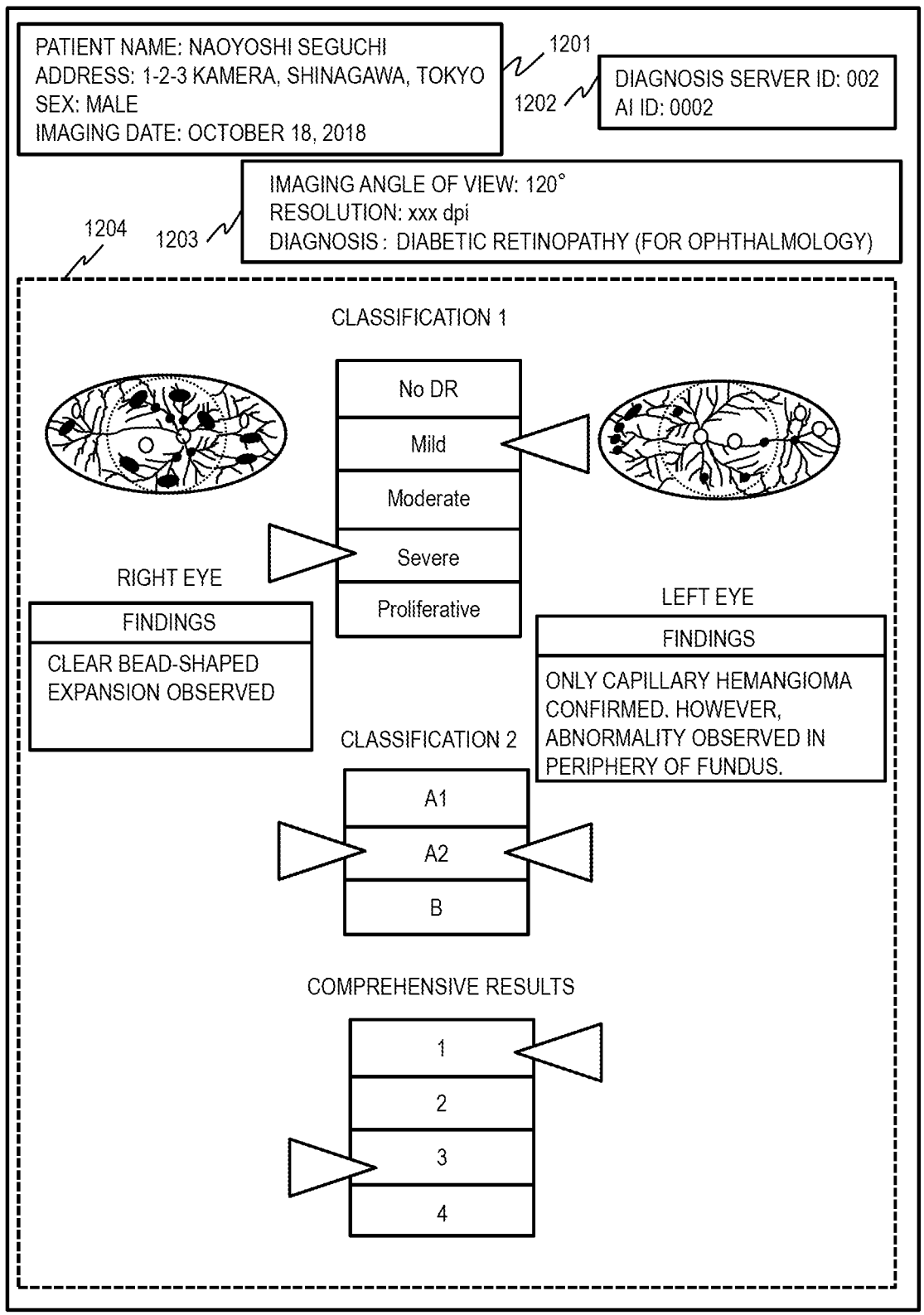
FIG. 15 illustrates an example of a display screen that displays a diagnosis result in a case where an image diagnosis is performed by a plurality of diagnosis servers according to the first embodiment.

The anonymized data for diagnosis may be sent to a plurality of diagnosis servers, that is, the image diagnosis for fundus image data may be performed by AIs having different image diagnosis models. FIG. 15 is an illustration of a display screen that displays a diagnosis result in a case where an image diagnosis is performed by a plurality of diagnosis servers. FIG. 15 illustrates an example of a display screen in a case where a diagnosis for the symptom level of diabetic retinopathy in wide-angle fundus image data captured at a wide angle of view is performed by two diagnosis servers. The types of classifications and number of classifications of the symptom levels indicated by the diagnosis result determined by the two diagnosis servers are different.

In this case, as illustrated in FIG. 15, a first diagnosis result determined by a diagnosis server equipped with an AI that performs image diagnosis for diabetic retinopathy based on a first classification scale (International Clinical Diabetic Retinopathy Disease Severity Scale classified into five grades) and a second diagnosis result determined by a diagnosis server equipped an AI that performs image diagnosis for diabetic retinopathy based on a second classification scale (Modified Davis Classification classified into three grades) are displayed in the diagnosis result display area 1204. In other words, symptom levels for diabetic retinopathy are displayed based on two different types of classification systems.

Further, for example, the display screen generation unit 103 of the administration server 100 may generate a symptom level in consideration of symptom levels based on different classification systems and display this symptom level as a comprehensive result.

Specifically, scores corresponding to symptom levels in different classification systems are preset (e.g., a score of 1 for No DR, 3 for Mild, . . . in the first classification scale, and a score of 1 for A1, 7 for A2, . . . in the second classification scale), and the display screen generation unit 103 outputs an average of the scores corresponding to the symptom levels for the left and right eyes.

In this compiled score, symptom levels corresponding to individual average score categories (a Symptom Level 1 if the score is more than 1 and less than 2.5, a Symptom Level 2 is the score is more than 2.5 and less than 5, etc.) are preset. The display screen generation unit 103 identifies the symptom level corresponding to the calculated average for the left eye and displays the identified symptom level in the diagnosis result display area 1204 as a comprehensive result. As a result, an AI diagnostic result for diabetic retinopathy can be integrated by multiple different classifications and a new index can be presented. Note that the second classification scale is not limited to the Modified Davis Classification and may be the Fukuda Classification.

In the present embodiment, the administration server 100 determines the diagnosis server that performs image diagnosis on the fundus image data included in the anonymized data for diagnosis, but another device (e.g., intra-hospital server 300, terminal 400, or imaging device 500) may determine the diagnosis server. In this case, the other device holds the AI selection information 110 and includes information (e.g., a flag) indicating the determined diagnosis server in the user data 703.

Second Embodiment

A diagnosis server 900 in an image diagnosis system according to a second embodiment includes a plurality of AIs 901 to 902. Differences to the first embodiment will be described.

Figure 16:
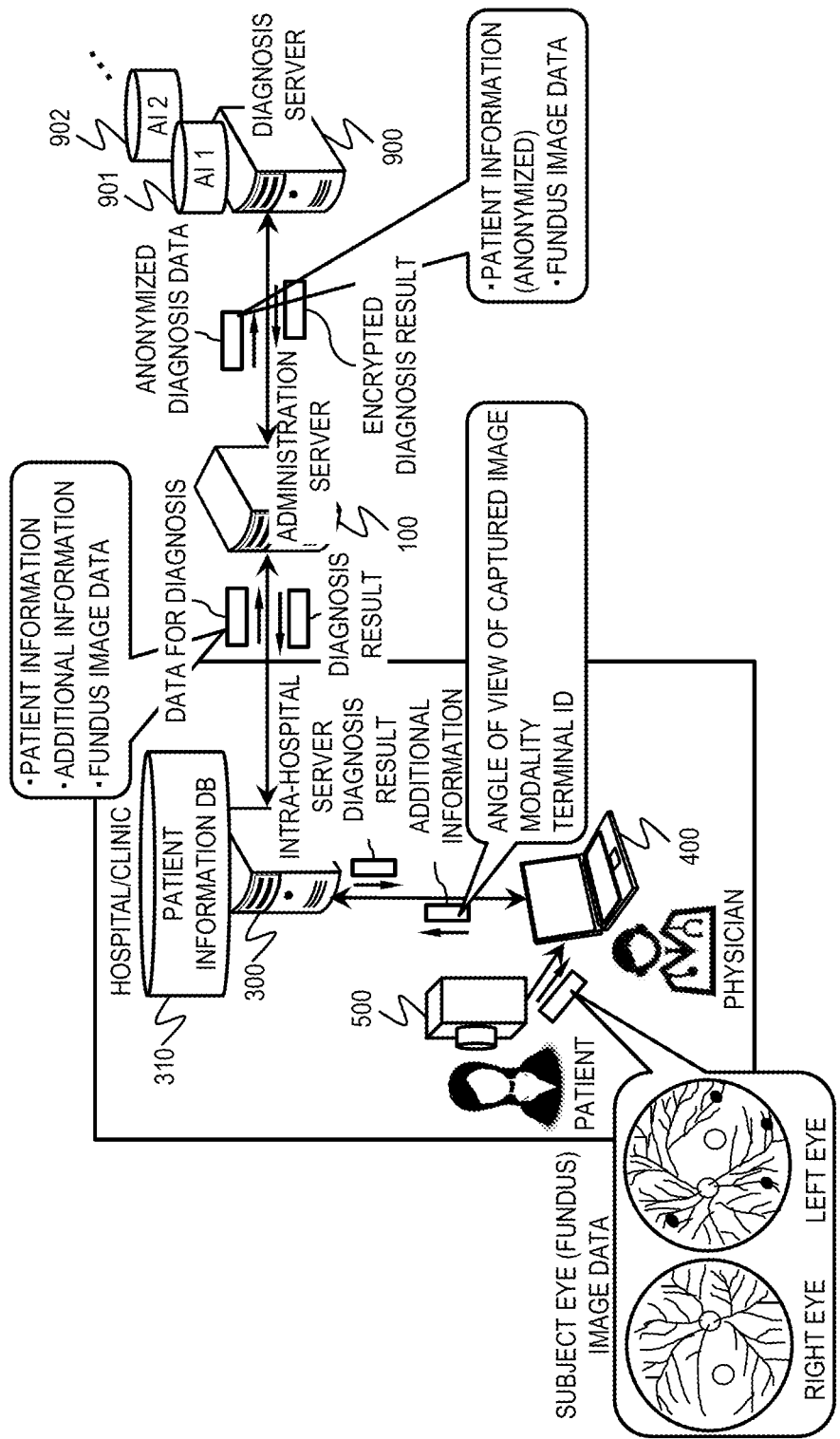
FIG. 16 is a diagram illustrating a configuration example of the image diagnosis system according to the second embodiment.

FIG. 16 is a diagram illustrating a configuration example of the image diagnosis system according to the second embodiment. This image diagnosis system differs from that illustrated in FIG. 1 in that the diagnosis server 900 includes a plurality of AIs. For the sake of brevity, in FIG. 16, the image diagnosis system includes one diagnosis server 900, but the image diagnosis system may include a plurality of diagnosis servers and some or all of the plurality of diagnosis servers may be equipped with a plurality of AIs. The plurality of AIs (AI 901 AI 902 or three or more AIs) each have a different image diagnosis model.

An AI selection information 110 according to the second embodiment includes information identifying an AI by using the additional information sent from the intra-hospital server 300 or the terminal 400. In other words, for example, the AI selection information 110 in FIG. 10 further includes an ID column for an AI. The ID for an AI is an ID that identifies an AI that performs image diagnosis on anonymized data for diagnosis corresponding to a value of the additional information.

Figure 17:
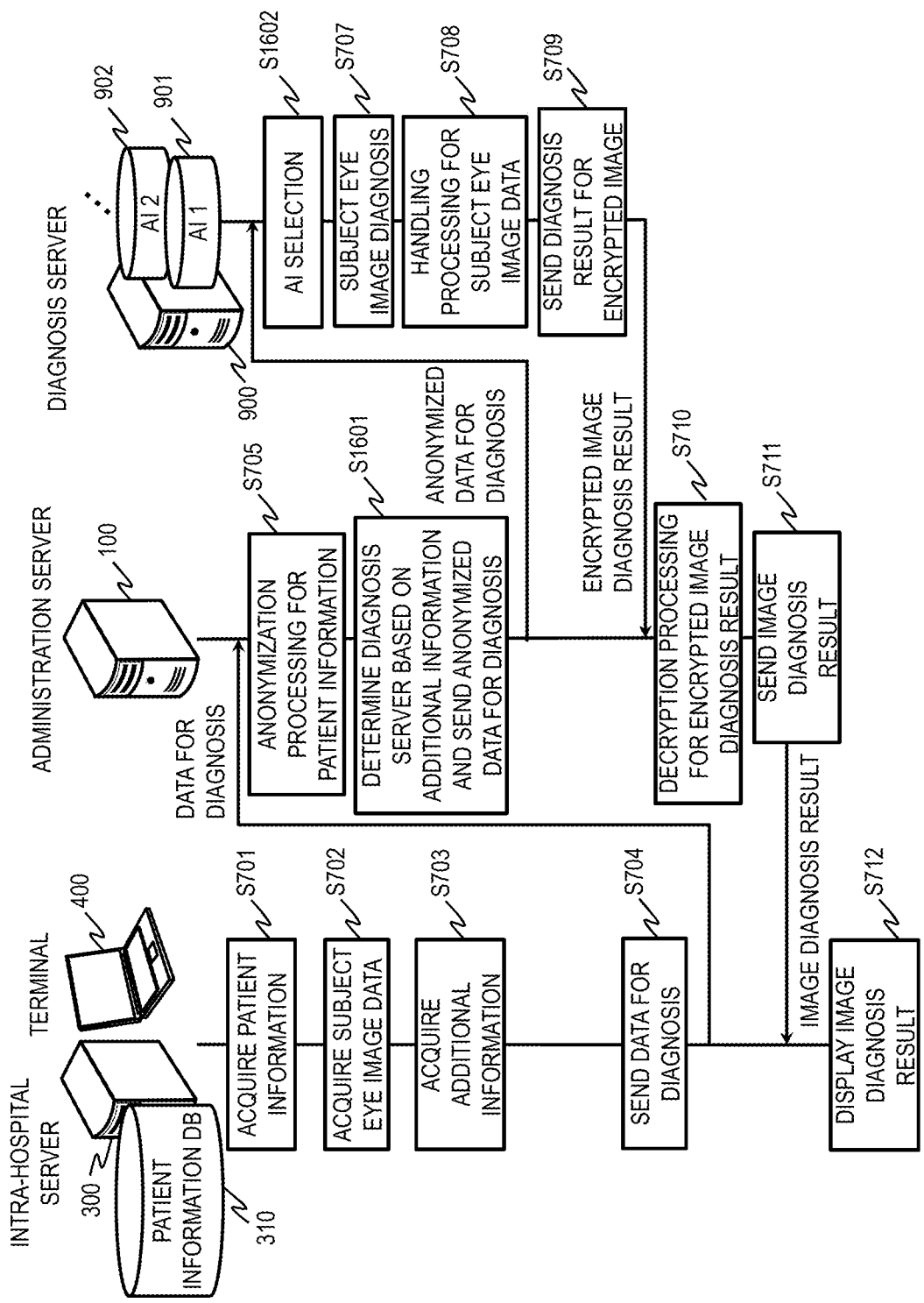
FIG. 17 is a sequence diagram illustrating image diagnosis processing by the image diagnosis system according to the second embodiment.

FIG. 17 is a sequence diagram illustrating image diagnosis processing by the image diagnosis system according to the second embodiment. Differences to FIG. 7 will be described. A Step S1601 is performed in place of Step S702. In Step S1601, the AI selection unit 102 of the administration server 100 selects at least one of the plurality of AIs (AI 901 AI 902 or three or more AIs) based on the AI selection information 110 and the additional information included in the received data for diagnosis.

Further, in Step S1601, the AI selection unit 102 includes AI information (e.g., the ID of the AI) indicating the selected AI 220 in the user data 703 and sends the anonymized data for diagnosis including the user data 703 to the selected diagnosis server equipped with the AI 220.

Then, the management unit of the diagnosis server that received the anonymized data for diagnosis selects the AI 220 indicated by the AI information included in the anonymized data for diagnosis and inputs the fundus image data included in the anonymized data for diagnosis to the selected AI 220 (S1602). Then, the processing moves to Step S707.

In the second embodiment, the administration server 100 determines the AI that performs the image diagnosis on the fundus image data included in the anonymized data for diagnosis, but another device (e.g., diagnosis server 900, intra-hospital server 300, terminal 400, or imaging device 500) may determine the AI. In this case, the other device holds the AI selection information 110. Further, the other device includes information (e.g., a flag) indicating the determined AI in the user data 703.

However, if the diagnosis server 900 determines the AI and the administration server 100 is unable to determine which diagnosis server 900 has the appropriate AI, the anonymized data for diagnosis is preferably sent to all diagnosis servers. Then, the diagnosis server 900 that has received the anonymized data for diagnosis refers to the AI selection information 110 to determine whether the image diagnosis on the fundus image data can be performed by the AI in the diagnosis server 900. If the diagnosis server determines that the diagnosis server is equipped with an AI that can perform the image diagnosis, the diagnosis result by AI is sent to the administration server 100.

The present invention is not limited to the above-described embodiments and these embodiments may be combined as desired. Further, other embodiments are included in the scope of the present invention without departing from the technical scope of the present invention.

EXPLANATION OF REFERENCES 100 administration server, 101 anonymization processing unit, 102 AI selection unit, 103 display screen generation unit, 104 diagnosis result data generation unit, 110 AI selection information, 201 diagnosis server, 2011 image diagnosis unit, 300 intra-hospital server, 301 anonymization processing unit, 302 patient information management unit, 303 display screen generation unit, 310 patient information DB, 400 terminal, 401 data for diagnosis generation unit, 402 additional information acquisition unit, 403 display screen generation unit, 600 calculator, 601 processor, 602 storage device, 603 input device, 604 output device, 605 communication if, 900 diagnosis server, 2021 training information management unit, 2031 diagnosis image generation unit, 2041 AI management unit, 2101 training DB, 2111 image diagnosis model

What is claimed is:

1. An information processing system comprising:
an image acquisition device configured to acquire subject eye image data of a patient; and
a first information processing device which can communicate with the image acquisition device and stores the subject eye image data,
the image acquisition device is configured to perform first transmission processing of transmitting, to the first information processing device, the subject eye image data and first transmission data which includes additional information used to identify an image diagnosis device configured to perform image diagnosis on the subject eye image data,
the first information processing device is configured to perform:
  storage processing of storing the subject eye image data when the first transmission data is received from the image acquisition device;
  identification processing of identifying, on the basis of the additional information, at least one of a first image diagnosis device that performs a first image diagnosis on the subject eye image data and a second image diagnosis device that performs a second image diagnosis different to the first image diagnosis on the subject eye image data; and
  second transmission processing of transmitting second transmission data including the subject eye image data to the identified image diagnosis device;
wherein the additional information is determined on the basis of attribute information of the subject eye image data,
wherein the attribute information includes information indicating resolution of the subject eye image data,
wherein, in the first image diagnosis, image diagnosis of the subject eye image data photographed at a first resolution is performed,
wherein, in the second image diagnosis, image diagnosis of the subject eye image data photographed at a second resolution that is higher than the first resolution is performed, and
the first image diagnosis device is configured to perform:
  include information recommending acquisition of the subject eye image data of the patient photographed at the second resolution in a diagnosis result of the image diagnosis in the first image diagnosis if detecting an abnormality in a subject eye of the patient in the subject eye image data; and
  transmit the diagnosis result to the first information processing device.

2. The information processing system according to claim 1, wherein:
a number of the image diagnosis devices including the first image diagnosis device and the second image diagnosis device is three or more;
the three or more image diagnosis devices can each perform different image diagnosis on the subject eye image data; and
the first information processing device is configured to identify at least one of the three or more image diagnosis devices in the identification processing.

3. The information processing system according to claim 1,
wherein the image acquisition device is configured to perform:
acquisition processing of acquiring the attribute information; and
determination processing of determining, as the additional information, a flag that identifies at least one of the first image diagnosis device and the second image diagnosis device on the basis of the acquired attribute information,
wherein, in the first transmission processing, the flag is transmitted to the first information processing device.

4. The information processing system according to claim 1, wherein:
the image acquisition device is configured to perform acquisition processing of acquiring the attribute information of the subject eye image data of the patient as the additional information, and
the first information processing device is configured to perform the identification processing on the basis of the received attribute information.

5. The information processing system according to claim 1,
wherein the attribute information includes imaging angle information indicating an imaging angle at which an image of the subject eye image data is photographed;
wherein, in the first image diagnosis, the image diagnosis on the subject eye image data photographed at a first imaging angle is performed, and
wherein, in the second image diagnosis, the image diagnosis on the subject eye image data photographed at a second imaging angle that is wider than the first imaging angle is performed.

6. The information processing system according to claim 5,
wherein the first image diagnosis device is configured to:
include information recommending acquisition of the subject eye image data of the patient photographed at the second imaging angle in a diagnosis result of the image diagnosis in the first image diagnosis if detecting an abnormality in the subject eye of the patient in the subject eye image data; and
transmit the diagnosis result to the first information processing device.

7. The information processing system according to claim 1,
wherein the subject eye image data includes at least one of fundus image data obtained by a fundus camera, fundus image data obtained by a scanning laser ophthalmoscope, and tomographic data obtained by optical coherence tomography.

8. The information processing system according to claim 7, wherein the subject eye image data includes fundus image data, and wherein, in the first image diagnosis and the second image diagnosis, diagnosis of a lesion in a fundus is performed.

9. The information processing system according to claim 8,
wherein, in the first image diagnosis and the second image diagnosis, diagnosis of diabetic retinopathy using the fundus image data is performed.

10. The information processing system according to claim 8, wherein:
the first image diagnosis indicates a diagnosis result of a first classification indicating a state of a lesion in the fundus;
the second image diagnosis indicates a diagnosis result of a second classification different to the first classification;
the first image diagnosis device is configured to transmit a first diagnosis result of the first classification in the first image diagnosis to the first information processing device;
the second image diagnosis device is configured to transmit a second diagnosis result of the second classification in the second image diagnosis to the first information processing device;
the first information processing device is configured to transmit the first diagnosis result and the second diagnosis result to the image acquisition device; and
the image acquisition device is configured to display a diagnosis result that is a combination of the first diagnosis result and the second diagnosis result.

11. The information processing system according to claim 1,
wherein the additional information identifies both the first image diagnosis device and the second image diagnosis device, and includes information that identifies an image diagnosis,
the first information processing device is configured to transmit the subject eye image data and the additional information to the first image diagnosis device and the second image diagnosis device, and
the first image diagnosis device and the second image diagnosis device are configured to perform image diagnosis indicated by the additional information on the received subject eye image data when being able to perform image diagnosis indicated by the additional information.

12. An information processing device comprising:
a processor, and
a memory device,
wherein the memory device holds:
subject eye image data of a patient;
additional information of the subject eye image data; and
correspondence information between the additional information and an image diagnosis device,
wherein the processor is configured to:
identify, on the basis of the correspondence information and the additional information, at least one of a first image diagnosis device that performs a first image diagnosis on the subject eye image data and a second image diagnosis device that performs a second image diagnosis different to the first image diagnosis on the subject eye image data;
transmit transmission data including the subject eye image data to the identified image diagnosis device, wherein the additional information is determined on the basis of attribute information of the subject eye image data, wherein the attribute information includes information indicating resolution of the subject eye image data, wherein, in the first image diagnosis, image diagnosis of the subject eye image data photographed at a first resolution is performed, wherein, in the second image diagnosis, image diagnosis of the subject eye image data photographed at a second resolution that is higher than the first resolution is performed;
include information recommending acquisition of the subject eye image data of the patient photographed at the second resolution in a diagnosis result of the image diagnosis in the first image diagnosis if detecting an abnormality in a subject eye of the patient in the subject eye image data; and transmit the diagnosis result to the first information processing device.

13. A method for processing information performed by an information processing device, the information processing device comprising:
a processor; and
a memory device,
wherein the memory device holds:
subject eye image data of a patient;
additional information of the subject eye image data; and
correspondence information between the additional information and an image diagnosis device, the method comprising:
identifying, by the processor, on the basis of the correspondence information and the additional information, at least one of a first image diagnosis device that performs a first image diagnosis on the subject eye image data and a second image diagnosis device that performs a second image diagnosis different to the first image diagnosis on the subject eye image data;

transmitting, by the processor, transmission data including the subject eye image data to the identified image diagnosis device, wherein the additional information is determined on the basis of attribute information of the subject eye image data, wherein the attribute information includes information indicating resolution of the subject eye image data, wherein, in the first image diagnosis, image diagnosis of the subject eye image data photographed at a first resolution is performed, wherein, in the second image diagnosis, image diagnosis of the subject eye image data photographed at a second resolution that is higher than the first resolution is performed;

including, by the processor, information recommending acquisition of the subject eye image data of the patient photographed at the second resolution in a diagnosis result of the image diagnosis in the first image diagnosis if detecting an abnormality in a subject eye of the patient in the subject eye image data; and transmitting, by the processor, the diagnosis result to the information processing device.

* * * * *